US008952036B2

(12) United States Patent
Rew

(10) Patent No.: US 8,952,036 B2
(45) Date of Patent: Feb. 10, 2015

(54) BENZOIC ACID DERIVATIVE MDM2 INHIBITOR FOR THE TREATMENT OF CANCER

(71) Applicant: Amgen Inc., Thousand Oaks, CA (US)

(72) Inventor: Yosup Rew, Foster City, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 14/192,553

(22) Filed: Feb. 27, 2014

(65) Prior Publication Data
US 2014/0243372 A1 Aug. 28, 2014

Related U.S. Application Data

(60) Provisional application No. 61/770,901, filed on Feb. 28, 2013.

(51) Int. Cl.
*A61K 31/45* (2006.01)
*C07D 211/76* (2006.01)
(52) U.S. Cl.
CPC .............. *A61K 31/45* (2013.01); *C07D 211/76* (2013.01)
USPC ......................................... 514/327; 546/222
(58) Field of Classification Search
USPC ......................................... 546/222; 514/327
See application file for complete search history.

(56) References Cited

U.S. PATENT DOCUMENTS

| 3,308,121 | A | 3/1967 | Gannon et al. |
| 5,334,720 | A | 8/1994 | Schmiesing et al. |
| 6,620,815 | B1 | 9/2003 | Lagu et al. |
| 7,425,638 | B2 | 9/2008 | Haley et al. |
| 7,776,875 | B2 | 8/2010 | Chen et al. |
| 8,569,341 | B2 | 10/2013 | Gribble, Jr. et al. |
| 2004/0186134 | A1 | 9/2004 | O'Connor et al. |
| 2007/0129416 | A1 | 6/2007 | Ding et al. |
| 2008/0280769 | A1 | 11/2008 | Doemling |
| 2009/0143364 | A1 | 6/2009 | Fotouhi et al. |
| 2009/0163512 | A1 | 6/2009 | Chen et al. |
| 2011/0319378 | A1 | 12/2011 | Bartberger et al. |
| 2014/0011796 | A1 | 1/2014 | Bartberger et al. |

FOREIGN PATENT DOCUMENTS

| CN | 102153557 A | 8/2011 |
| DE | 3246148 A1 | 6/1984 |
| WO | WO95/23135 A1 | 8/1995 |
| WO | WO96/06095 A1 | 2/1996 |
| WO | WO97/30045 A1 | 8/1997 |
| WO | WO99/06397 A2 | 2/1999 |
| WO | WO99/31507 A1 | 6/1999 |
| WO | WO02/17912 A1 | 3/2002 |
| WO | WO02/089738 A2 | 11/2002 |
| WO | WO02/094787 A1 | 11/2002 |
| WO | WO03/051359 A1 | 6/2003 |
| WO | WO2004/031149 A1 | 4/2004 |
| WO | WO2005/110996 A1 | 11/2005 |
| WO | WO2005/123691 A1 | 12/2005 |
| WO | WO2006/097261 A1 | 9/2006 |
| WO | WO2006/107859 A2 | 10/2006 |
| WO | WO2006/107860 A2 | 10/2006 |
| WO | WO2007/063013 A1 | 6/2007 |
| WO | WO2007/104664 A1 | 9/2007 |
| WO | WO2008/005268 A1 | 1/2008 |
| WO | WO2008/010953 A2 | 1/2008 |
| WO | WO2008/021338 A2 | 2/2008 |
| WO | WO2008/021339 A2 | 2/2008 |
| WO | WO2008/076754 A2 | 6/2008 |
| WO | WO2008/110793 A1 | 9/2008 |
| WO | WO2008/125487 A1 | 10/2008 |
| WO | WO2008/141975 A1 | 11/2008 |
| WO | WO2009/004430 A1 | 1/2009 |
| WO | WO2009/047161 A1 | 4/2009 |
| WO | WO2009/082038 A2 | 7/2009 |
| WO | WO2009/114950 A1 | 9/2009 |
| WO | WO2009/156735 A2 | 12/2009 |
| WO | WO2010/028862 A1 | 3/2010 |
| WO | WO2010/031713 A1 | 3/2010 |
| WO | WO2010/121995 A1 | 10/2010 |
| WO | WO2011/023677 A1 | 3/2011 |
| WO | WO2011/067185 A1 | 6/2011 |
| WO | WO2011/076786 A1 | 6/2011 |
| WO | WO2013/049250 A1 | 4/2013 |

OTHER PUBLICATIONS

Rew, J Med Chem, vol. 55, pp. 4936-4954, 2012.*
N.J. Anthony, Pseudo-Allylic $A_{1,3}$ Strain as a Conformational Control Element: Stereoselective Syntheses of $\psi[CH_2O]$ Pseudodipeptides, Tetrahedron Letters, vol. 36, No. 22, pp. 3821-3824, 1995.
Uli Rothweiler, Isoquinolin-1-one Inhibitors of the MDM2-p53 Interaction, ChemMedChem 2008, vol. 3, pp. 1118-1128.
International Search Report, PCT/US2011/039184, Issued Sep. 9, 2011, pp. 1-3.
Written Opinion of the International Searching Authority, PCT/US2011/039814, Issued Sep. 9, 2011, pp. 1-5.
Allen, John G., Discovery and Optimization of Chromenotriazolopyrimidines as Potent Inhibitors of the Mouse Double Minute 2-Tumor Protein 53 Protein-Protein Interaction, Journal of Medicinal Chemistry, Nov. 26, 2009;52(22): pp. 7044-7053.

(Continued)

*Primary Examiner* — D M Seaman
(74) *Attorney, Agent, or Firm* — Joseph W. Bulock; Todd M. Crissey

(57) ABSTRACT

The present invention provides a MDM2 inhibitor compound, or a pharmaceutically acceptable salt thereof, which compound is useful as a therapeutic agent, particularly for the treatment of cancers. The present invention also relates to pharmaceutical compositions that contains the MDM2 inhibitor.

39 Claims, 1 Drawing Sheet

(56) References Cited

OTHER PUBLICATIONS

Rew, Yosup, Structure-Based Design of Novel Inhibitors of the MDM2-p53 Interaction, Journal of Medicinal Chemistry, Jun. 14, 2012;55(11): pp. 4936-4954. E-published May 9, 2012.

Michelsen, Klaus, Ordering of the N-Terminus of Human MDM2 by Small Molecule Inhibitors, Journal American Chemical Society, Oct. 17, 2012;134(41): pp. 17059-17067. Epublished Oct. 5, 2012.

Written Opinion of the International Starching Authority, PCT/US2012/057389, Issued Jan. 18, 2013, pp. 1-6.

International Search Report of the International Searching Authority, PCT/US2012/057389, Issued Jan. 18, 2013, pp. 1-4.

J.L. Garcia Ruano et al., "Synthesis of 2-phenyl-, 3-phenyl-, cis-2,3-diphenyl-, and trans-2,3-diphenyl-1, 4-thiazanes and derivatives (N-methyl, N-alkoxycarbonyl, S-oxides, and S, S-dioxides)", 1992.

* cited by examiner

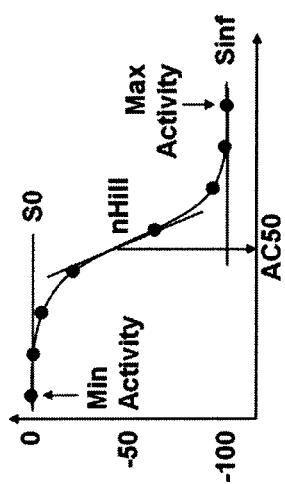

BENZOIC ACID DERIVATIVE MDM2 INHIBITOR FOR THE TREATMENT OF CANCER

CROSS-REFERENCE TO RELATED APPLICATION

This application claims priority of U.S. provisional patent application No. 61/770,901, filed 28 Feb. 2013, the contents of which are incorporated by reference herein in their entirety.

FIELD OF THE INVENTION

The present invention relates a MDM2 inhibitor that is useful as therapeutic agent, particularly for the treatment of cancers. The invention also relates to pharmaceutical compositions that contain the MDM2 inhibitor.

BACKGROUND OF THE INVENTION p53 is a tumor suppressor and transcription factor that responds to cellular stress by activating the transcription of numerous genes involved in cell cycle arrest, apoptosis, senescence, and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. In support of this notion, three groups of investigators have used mouse models to demonstrate that absence of p53 function is a continuous requirement for the maintenance of established tumors. When the investigators restored p53 function to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, p14ARF. It has been suggested that alterations downstream of p53 may be responsible for at least partially inactivating the p53 pathway in $p53^{WT}$ tumors (p53 wildtype). In support of this concept, some $p53^{WT}$ tumors appear to exhibit reduced apoptotic capacity, although their capacity to undergo cell cycle arrest remains intact. One cancer treatment strategy involves the use of small molecules that bind MDM2 and neutralize its interaction with p53. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm. All three of these mechanisms would be blocked by neutralizing the MDM2-p53 interaction. In particular, this therapeutic strategy could be applied to tumors that are $p53^{WT}$, and studies with small molecule MDM2 inhibitors have yielded promising reductions in tumor growth both in vitro and in vivo. Further, in patients with p53-inactivated tumors, stabilization of wildtype p53 in normal tissues by MDM2 inhibition might allow selective protection of normal tissues from mitotic poisons.

The present invention relates to a compound capable of inhibiting the interaction between p53 and MDM2 and activating p53 downstream effector genes. As such, the compound of the present invention would be useful in the treatment of cancers, bacterial infections, viral infections, ulcers and inflammation. In particular, the compound of the present invention is useful to treat solid tumors such as: breast, colon, lung and prostate tumors; and liquid tumors such as lymphomas and leukemias. As used herein, MDM2 means a human MDM2 protein and p53 means a human p53 protein. It is noted that human MDM2 can also be referred to as HDM2 or hMDM2.

SUMMARY OF THE INVENTION

In embodiment 1, the present invention provides the compound

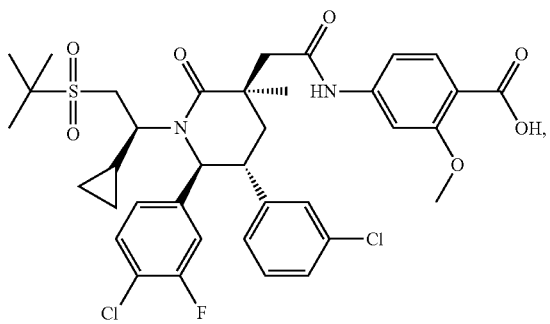 [SMILES: COc1cc(NC(=O)C[C@@]2(C)C[C@H](c3cccc(Cl)c3)[C@@H](c3ccc(Cl)c(F)c3)N([C@H](CS(=O)(=O)C(C)(C)C)C3CC3)C2=O)ccc1C(=O)O]

or a pharmaceutically acceptable salt thereof.

In embodiment 2, the present invention provides the compound

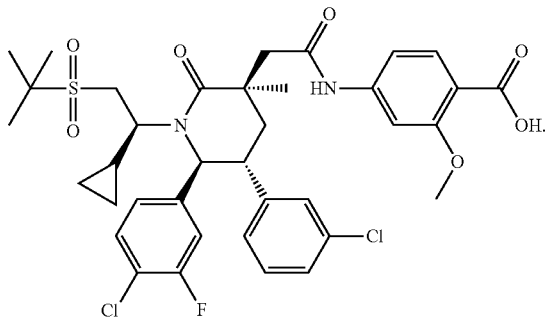 [SMILES: COc1cc(NC(=O)C[C@@]2(C)C[C@H](c3cccc(Cl)c3)[C@@H](c3ccc(Cl)c(F)c3)N([C@H](CS(=O)(=O)C(C)(C)C)C3CC3)C2=O)ccc1C(=O)O]

In embodiment 3, the present invention provides pharmaceutical compositions comprising a compound of any one of embodiments 1 or 2, and a pharmaceutically acceptable excipient.

In embodiment 4, the present invention provides methods of treating cancer in a subject in need thereof, the methods comprising administering to the subject an effective dosage amount of a compound according to any one of embodiments 1 to 2.

In embodiment 5, the present invention provides methods of embodiment 4, wherein the cancer is selected from bladder, breast, colon, rectum, kidney, liver, small cell lung cancer, non-small-cell lung cancer, esophagus, gall-bladder, ovary, pancreas, stomach, cervix, thyroid, prostate, skin, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, acute or chronic myelogenous leukemia, melanoma, endometrial cancer, head and neck cancer, glioblastoma, or osteosarcoma.

In embodiment 6, the present invention provides methods of embodiment 4, wherein the cancer is bladder cancer.

In embodiment 7, the present invention provides methods of embodiment 4, wherein the cancer is breast cancer.

In embodiment 8, the present invention provides methods of embodiment 4, wherein the cancer is colon cancer.

In embodiment 9, the present invention provides methods of embodiment 4, wherein the cancer is rectum cancer.

In embodiment 10, the present invention provides methods of embodiment 4, wherein the cancer is kidney cancer.

In embodiment 11, the present invention provides methods of embodiment 4, wherein the cancer is liver cancer.

In embodiment 12, the present invention provides methods of embodiment 4, wherein the cancer is small cell lung cancer.

In embodiment 13, the present invention provides methods of embodiment 4, wherein the cancer is non-small-cell lung cancer.

In embodiment 14, the present invention provides methods of embodiment 4, wherein the cancer is esophagus cancer.

In embodiment 15, the present invention provides methods of embodiment 4, wherein the cancer is gall-bladder cancer.

In embodiment 16, the present invention provides methods of embodiment 4, wherein the cancer is ovary cancer.

In embodiment 17, the present invention provides methods of embodiment 4, wherein the cancer is pancreas cancer.

In embodiment 18, the present invention provides methods of embodiment 4, wherein the cancer is stomach cancer.

In embodiment 19, the present invention provides methods of embodiment 4, wherein the cancer is cervix cancer.

In embodiment 20, the present invention provides methods of embodiment 4, wherein the cancer is thyroid cancer.

In embodiment 21, the present invention provides methods of embodiment 4, wherein the cancer is prostate cancer.

In embodiment 22, the present invention provides methods of embodiment 4, wherein the cancer is skin cancer.

In embodiment 23, the present invention provides methods of embodiment 4, wherein the cancer is acute lymphocytic leukemia.

In embodiment 24, the present invention provides methods of embodiment 4, wherein the cancer is chronic myelogenous leukemia.

In embodiment 25, the present invention provides methods of embodiment 4, wherein the cancer is acute lymphoblastic leukemia.

In embodiment 26, the present invention provides methods of embodiment 4, wherein the cancer is B-cell lymphoma.

In embodiment 27, the present invention provides methods of embodiment 4, wherein the cancer is T-cell-lymphoma.

In embodiment 28, the present invention provides methods of embodiment 4, wherein the cancer is Hodgkin's lymphoma.

In embodiment 29, the present invention provides methods of embodiment 4, wherein the cancer is non-Hodgkin's lymphoma.

In embodiment 30, the present invention provides methods of embodiment 4, wherein the cancer is hairy cell lymphoma.

In embodiment 31, the present invention provides methods of embodiment 4, wherein the cancer is Burkett's lymphoma.

In embodiment 32, the present invention provides methods of embodiment 4, wherein the cancer is acute myelogenous leukemia.

In embodiment 33, the present invention provides methods of embodiment 4, wherein the cancer is chronic myelogenous leukemia.

In embodiment 34, the present invention provides methods of embodiment 4, wherein the cancer is melanoma.

In embodiment 35, the present invention provides methods of embodiment 4, wherein the cancer is endometrial cancer.

In embodiment 36, the present invention provides methods of embodiment 4, wherein the cancer is head and neck cancer.

In embodiment 37, the present invention provides methods of embodiment 4, wherein the cancer is glioblastoma.

In embodiment 38, the present invention provides methods of embodiment 4, wherein the cancer is osteosarcoma.

In embodiment 39, the present invention provides methods of any one of embodiments 4 or 6 to 38, wherein the cancer is identified as p53 wildtype.

BRIEF DESCRIPTION OF THE DRAWINGS

FIG. 1 shows the four-parameter logical Hill model for curve fitting.

DETAILED DESCRIPTION OF THE INVENTION

The present invention provides a MDM2 inhibitor that is useful as therapeutic agent, particularly for the treatment of cancers. The invention also relates to pharmaceutical compositions that contain the MDM2 inhibitor.

The symbol "—" represents a covalent bond and can also be used in a radical group to indicate the point of attachment to another group. In chemical structures, the symbol is commonly used to represent a methyl group in a molecule.

The term "comprising" is meant to be open ended, including the indicated component but not excluding other elements.

The term "therapeutically effective amount" means an amount of a compound that ameliorates, attenuates or eliminates one or more symptom of a particular disease or condition, or prevents or delays the onset of one of more symptom of a particular disease or condition.

The terms "patient" and "subject" may be used interchangeably and mean animals, such as dogs, cats, cows, horses, sheep and humans. Particular patients are mammals. The term patient includes males and females.

The term "pharmaceutically acceptable" means that the referenced substance, such as a compound of the present invention, or a salt of the compound, or a formulation containing the compound, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compound of the present invention is administered to a patient in a therapeutically effective amount. The compound can be administered alone or as part of a pharmaceutically acceptable composition or formulation. In addition, the compound or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compound of the present invention can be administered alone or in combination with other pharmaceutically active compounds. The other pharmaceutically active compounds can be intended to treat the same disease or condition as the compound of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

The term "cancer" means a physiological condition in mammals that is characterized by unregulated cell growth. General classes of cancers include carcinomas, lymphomas, sarcomas, and blastomas.

The compound of the present invention can be used to treat cancer. The methods of treating a cancer comprise administering to a patient in need thereof a therapeutically effective amount of the compound, or a pharmaceutically acceptable salt thereof.

The compound of the present invention can be used to treat tumors. The methods of treating a tumor comprise administering to a patient in need thereof a therapeutically effective amount of the compound, or a pharmaceutically acceptable salt thereof.

The invention also concerns the use of the compound of the present invention in the manufacture of a medicament for the treatment of a condition such as a cancer.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with the compound of the present invention include endometrial cancer, head and neck cancer, glioblastoma, malignant ascites, and hematopoietic cancers.

Particular cancers that can be treated by the compounds of the present invention include soft tissue sarcomas, bone cancers such as osteosarcoma, breast tumors, bladder cancer, Li-Fraumeni syndrome, brain tumors, rhabdomyosarcoma, adrenocortical carcinoma, colorectal cancer, non-small cell lung cancer, and acute myeleogenous leukemia (AML).

In a particular embodiment of the invention that relates to the treatment of cancers, the cancer is identified as p53wildtype ($p53^{WT}$). In another particular embodiment, the cancer is identified as $p53^{WT}$ and CDKN2A mutant. In another aspect, the present invention provides a diagnostic for determining which patients should be administered a compound of the present invention. For example, a sample of a patient's cancer cells may be taken and analyzed to determine the status of the cancer cells with respect to p53 and/or CDKN2A. In one aspect, a patient having a cancer that is $p53^{WT}$ will be selected for treatment over patients having a cancer that is mutated with respect to p53. In another aspect, a patient having a cancer that is both $p53^{WT}$ and has a mutant CDNK2A protein is selected over a patient that does not have these characteristics. The taking of a cancer cells for analyses is well known to those skilled in the art. The term "$p53^{WT}$" means a protein encoded by genomic DNA sequence no. NC_000017 version 9 (7512445.7531642) (GenBank); a protein encoded by cDNA sequence no. NM_000546 (GenBank); or a protein having the GenBank sequence no. NP_000537.3. The term "CDNK2A mutant" means a CDNK2A protein that in not wildtype. The term "CDKN2A wildtype" means a protein encoded by genomic DNA sequence no. 9:21957751-21984490 (Ensembl ID); a protein encoded by cDNA sequence no. NM_000077 (GenBank) or NM_058195 9GenBank) or; or a protein having the GenBank sequence no. NP_000068 or NP_478102.

The compounds of the present invention can also be used to treat hyperproliferative disorders such as thyroid hyperplasia (especially Grave's disease), and cysts (such as hypervascularity of ovarian stroma, characteristic of polycystic ovarian syndrome (Stein-Leventhal syndrome)).

The compound of the present invention can also be used to treat the following diseases or conditions: asthma, chronic obstructive pulmonary disease (COPD), emphysema, psoriasis, contact dermatitis, conjunctivitis, allergic rhinitis, systemic lupus erythematosus (SLE), ulcerative colitis, Crohn's disease, multiple sclerosis, rheumatoid arthritis, inflammatory bowel disease, Alzheimer's disease, atherosclerosis and Huntington's disease.

The compound of the present invention can also be used to treat inflammatory diseases, hypoxia, ulcers, viral infections, bacterial infections, and bacterial sepsis.

The compound of the present invention, or the pharmaceutically acceptable salts thereof, may also be administered in combination with one or more additional pharmaceutically active compounds/agents. In a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; pacitaxel; thioguanine; idarubicin; dactinomycin; imatinib; gemcitabine; altretamine; asparaginase; bleomycin; capecitabine; carmustine; cladisat. aq. NaCl solution; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine;

desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Additional pharmaceutically active agents that can be used in the treatment of cancers and that can be used in combination with the compound of the present invention include: vascular endothelial growth factor (VEGF) inhibitors, hepatocyte growth factor/scatter factor (HGF/SF) inhibitors, angiopoietin 1 and/or 2 inhibitors, tumor necrosis factor-related apoptosis-inducing ligand (TRAIL) agonists, recombinant human apo2 ligand (TRAIL), insulin-like growth factor 1 receptor (IGFR-1) inhibitors, cFMS inhibitors, HER 2 inhibitors, c-met inhibitors, aurora kinase inhibitors, CDK 4 and/or 6 inhibitors, and B-raf inhibitors.

Further additional pharmaceutically active agents that can be used in the treatment of cancers and that can be used in combination with the compound of the present invention include antibody drug conjugates (ADCs) whereby an antibody that binds to a protein, preferably on a cancer cell, is conjugated using a linker with a chemical compound that is detrimental to the cancer cell. Examples of chemical compounds that are detrimental to a cancer cell include maytansinoids derivatives and auristatin derivatives.

Still further additional pharmaceutically active agents that can be used in the treatment of cancers and that can be used in combination with the compound of the present invention include: epoetin alfa; darbepoetin alfa; panitumumab; pegfilgrastim; palifermin; filgrastim; denosumab; ancestim; AMG 102; AMG 319; AMG 386; AMG 479 (Ganitumab); AMG 511, AMG 900, AMG 655 (Conatumumab); AMG 745; AMG 951; and AMG 706 (Motesanib), or a pharmaceutically acceptable salt thereof.

In another aspect, the present invention relates to the use of the compound of the present invention in combination with one or more pharmaceutical agent that is an inhibitor of a protein in the phosphatidylinositol 3-kinase (PI3K) pathway. Combinations of compounds of the present invention along with inhibitors of proteins in the PI3K pathway have shown synergy in cancer cell growth assays, including enhanced apoptosis and cell killing. Examples of proteins in the PI3K pathway include PI3K, mTOR and PKB (also known as Akt). The PI3K protein exists in several isoforms including α, β, δ, or γ. It is contemplated that a PI3K inhibitor that can be used in combination with a compound of the present invention can be selective for one or more isoform. By selective it is meant that the compounds inhibit one or more isoform more that other isoforms. Selectivity is a concept well known to those is the art and can be measured with well known activity in vitro or cell-based assays. Preferred selectivity includes greater than 2-fold, preferably 10-fold, or more preferably 100-fold greater selectivity for one or more isoform over the other isoforms. In one aspect, the PI3K inhibitors that can be used in combination with compounds of the present invention is a PI3K α selective inhibitor. In another aspect the compound is a PI3K δ selective inhibitor.

Examples of PI3K inhibitors that can be used in combination with one or more compounds of the present invention include those disclosed in the following: PCT published application no. WO2010/151791; PCT published application no. WO2010/151737; PCT published application no. WO2010/151735; PCT published application no. WO2010151740; PCT published application no. WO2008/118455; PCT published application no. WO2008/118454; PCT published application no. WO2008/118468; U.S. published application no. US20100331293; U.S. published application no. US20100331306; U.S. published application no. US20090023761; U.S. published application no. US20090030002; U.S. published application no. US20090137581;U.S. published application no. US2009/0054405; U.S. published application no. U.S. 2009/0163489; U.S. published application no. US 2010/0273764; U.S. published application no. U.S. 2011/0092504; or PCT published application no. WO2010/108074.

Preferred PI3K inhibitors for use in combination with the compound of the present invention include:

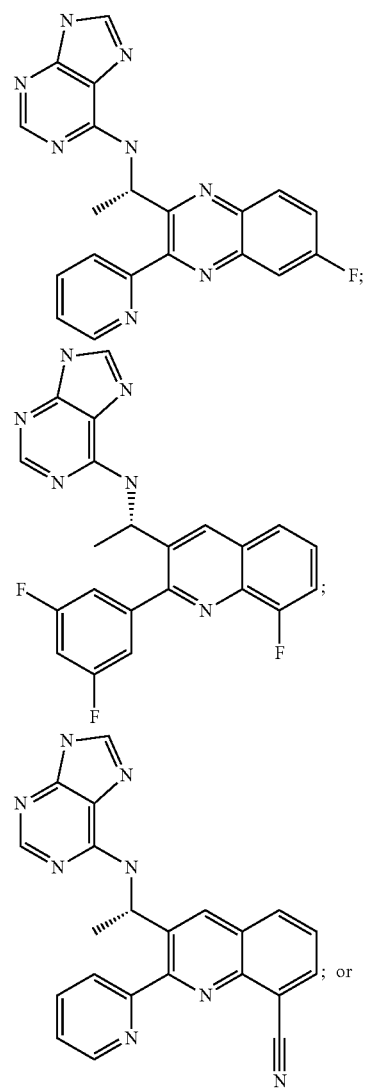

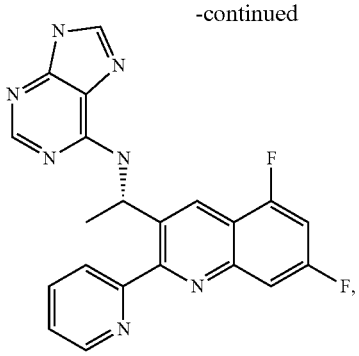

or a pharmaceutically acceptable salt thereof.

Also preferred is a compound of Formula IIa below, or a pharmaceutically acceptable salt thereof, IIa

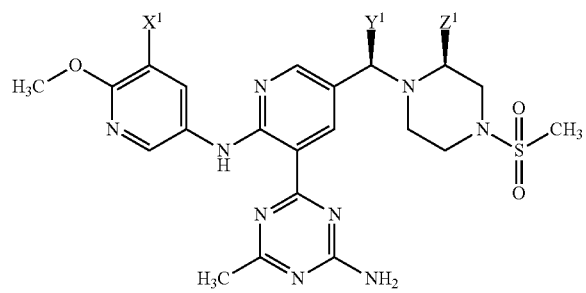

wherein $X^1$ is fluorine or hydrogen; $Y^1$ is hydrogen or methyl; and $Z^1$ is hydrogen or methyl.

Compounds that inhibit both PI3K and mTOR (dual inhibitors) are known. In still another aspect, the present invention provides the use of dual PI3K and mTOR inhibitors for use in combination with the compound of the present invention.

mTOR is a protein in the PI3K pathway. It is another aspect of the present invention to use an mTOR inhibitor in combination with the compound of the present invention. mTOR inhibitors that can be used in combination with the compound of the present invention include those disclosed in the following documents: PCT published application no. WO2010/132598 or PCT published application no. WO2010/096314.

PKB (Akt) is also a protein in the PI3K pathway. It is another aspect of the present invention to use an mTOR inhibitor in combination with the compound of the present invention. PKB inhibitors that can be used in combination with the compound of the present invention include those disclosed in the following documents: U.S. Pat. Nos. 7,354,944; 7,700,636; 7,919,514; 7,514,566; U.S. patent application publication no. US 2009/0270445 A1; U.S. Pat. Nos. 7,919,504; 7,897,619; or PCT published application no. WO 2010/083246 A1.

The compound of the present invention can be used in combination with CDK4 and/or 6 inhibitors. CDK 4 and/or 6 inhibitors that can be used in combination with the compound of the present invention include those disclosed in the following documents: PCT published application no. WO 2009/085185 or U.S. patent application publication no. US2011/0097305.

The compound of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, the compound of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofiran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SD01 (Amgen); galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (Pfizer); TA 077 (Tanabe); tetrathiomolybdate; thaliblastine; thrombopoietin;

tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar. It is noted that the agents recited above may also be administered as pharmaceutically acceptable salts when appropriate.

The compound of the present invention may also be used in combination with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: the compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, ... etc. ... Second Week, Monday, Tuesday, ... " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compound of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compound can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of the compound of the present invention include ointments, powders, sprays and inhalants. The active compound or compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compound of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compound of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compound of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compound of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compound of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, because the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

The compound of the present invention may contain asymmetric or chiral centers, and therefore, exist in different stereoisomeric forms. It is contemplated that all stereoisomeric forms of the compound as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compound of the present invention may exist in unsolvated as well as solvated forms with pharmaceutically acceptable solvents such as water (hydrate), ethanol, and the like. The present invention contemplates and encompasses both the solvated and unsolvated forms.

It is also possible that the compound of the present invention may exist in different tautomeric forms. All tautomers of the compound of the present invention are contemplated. For example, all of the tautomeric forms of the tetrazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise. It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{18}O$, $^{31}P$, $^{32}P$, $^{35}S$, $^{18}F$, and $^{36}Cl$. In one aspect, the present invention relates to compounds wherein one or more hydrogen atom is replaced with deuterium ($^{2}H$) atoms.

The compound of the present invention that contains the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compound of the present invention may exist in various solid states including crystalline states and as an amorphous state. The different crystalline states, also called polymorphs, and the amorphous states of the present compounds are contemplated as part of this invention.

In synthesizing the compound of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents, published patent applications and other publications recited herein are hereby incorporated by reference.

The examples presented below illustrate specific embodiments of the present invention. These examples are meant to be representative and are not intended to limit the scope of the claims in any manner. Unless otherwise noted, when a percent is used herein with respect to a solid, the percent is by weight with respect to the referenced solid composition. When a percent is used herein with respect to a liquid, the percent is by volume with respect to the referenced solution.

$^{1}$H-NMR spectra were acquired with a 500 MHz Bruker Avance III spectrometer system (Bruker Biospin, Billerica, Mass.) equipped with a Bruker 5-mm z-axis gradient BBI probe; or with a 400 MHz Bruker Avance II or Avance III spectrometer system equipped with a Bruker 5-mm z-axis gradient BBO probe. Samples were typically dissolved in 600 μL of either DMSO-$d_6$ or $CD_3OD$ for NMR analysis. $^{1}$H chemical shifts are referenced relative to the residual proton signals from the deuterated solvents used for the analysis at d 2.50 ppm for DMSO-$d_6$ and d 3.30 ppm for $CD_3OD$.

Significant peaks are tabulated and typically include: number of protons, multiplicity (s, singlet; d, doublet; dd, doublet of doublets; t, triplet; q, quartet; m, multiplet; br s, broad singlet) and coupling constant(s) in Hertz.

Electron Ionization (EI) mass spectra were typically recorded on an Agilent Technologies 6140 Quadrupole LC/MS mass spectrometer. Mass spectrometry results are reported as the ratio of mass over charge, sometimes followed by the relative abundance of each ion (in parentheses). Starting materials in the Examples below are typically either available from commercial sources such as Sigma-Aldrich, St. Louis, Mo., or via literature procedures.

The following abbreviations may be used herein:

~about
+ve or pos. ion positive ion
Δ heat
Ac acetyl
$Ac_2O$ acetic anhydride
aq aqueous
AcOH acetic acid
Bn benzyl
Boc tert-butyloxycarbonyl
BSA bovine serum albumin
Bu butyl
Bz benzoyl
Calcd or Calc'd calculated
Conc. concentrated
CSA camphor-10-sulfonic acid
d day(s)
DBU 1,8-diazabicyclo[5.4.0]undec-7-ene
DCE dichloroethane
DCM dichloromethane
DDQ 2,3-dichloro-5,6-dicyano-1,4-benzoquinone
DEA diethylamine Dess-Martin periodinane;
Dess-Martin reagent 1,1,1-triacetoxy-1,1-dihydro-1,2-benziodoxol-3-(1H)-one
DIEA or DIPEA diisopropylethylamine
DMAP 4-dimethylaminopyridine
DME 1,2-dimethoxyethane
DMF N,N-dimethylformamide
DMSO dimethyl sulfoxide
DPPA diphenylphosphoryl azide
dr diastereomeric ratio
DTT dithiothreitol
DVB divinylbenzene
EDC N-ethyl-N'-(3-dimethylaminopropyl)carbodiimide
ee or e.e. enantiomeric excess
eq equivalent
ESI or ES electrospray ionization
Et ethyl
$Et_2O$ diethyl ether
$Et_3N$ triethylamine
EtOAc ethyl acetate
EtOH ethyl alcohol
g gram(s)
h hour(s)
HATU O-(7-azabenzotriazol-1-yl)-N,N,N',N'tetramethyluronium hexafluorophosphate
HBTU O-benzotriazole-N,N,N',N'-tetramethyl-uronium-hexafluorophosphate
Hex hexanes
HMPA hexamethylphosphoramide
HOAt 1-hydroxy-7-azabenzotriazole
HOBt hydroxybenzotriazole
HPLC high pressure liquid chromatography
IPA or iPrOH isopropyl alcohol
Jones reagent solution of chromium(IV)oxide and sulfuric acid in water
KHMDS potassium hexamethyldisilazide
KOAc potassium acetate
LCMS, LC-MS or LC/MS liquid chromatography mass spectrometry
LDA lithium diisopropylamide
LHMDS or LiHMDS lithium hexamethyldisilazide
L-Selectride® lithium tri-sec-butylborohydride (Sigma-Aldrich, St. Louis)
M molar (mol $L^{-1}$)
mCPBA m-chloroperoxybenzoic acid
Me methyl
MeCN acetonitrile
MeI iodomethane
MeOH methyl alcohol
mg milligram(s)
min minute(s)
mL milliliter(s)
M mole(s)
MS mass spectrometry
MsCl methanesulfonyl chloride
MTBE or MtBE methyl tert-butyl ether
m/z mass-to-charge ratio
NaHMDS sodium hexamethyldisilazide
NaOtBu sodium tert-butoxide
NBS N-bromosuccinimide
nBuLi n-butyl lithium
NMO N-methylmorpholine-N-oxide
NMP 1-methyl-2-pyrrolidinone
NMR nuclear magnetic resonance
N-Selectride® sodium tri-sec-butylborohydride (Sigma-Aldrich, St. Louis)
PBS phosphate buffered saline
PMB paramethoxybenzyl
Pr propyl
ppm parts per million
PTFE polytetrafluoroethylene
p-tol para-toluoyl
rac racemic
RP-HPLC or RPHPLC reversed phase high pressure liquid chromatography
RT or rt or r.t. room temperature
$RuCl_2$(S-binap)(S-DAIPEN) dichloro{(S)-(−)-2,2'-bis[di(3,5-xylyl)phosphino]-1,1'-binaphthyl][(2S)-(+)-1,1-bis(4-methoxyphenyl)-3-methyl-1,2-butanediamine]ruthenium (II)
sat. or sat'd or satd saturated
SFC supercritical fluid chromatography
TBAF tetrabutylammonium fluoride
TBDMS tert-butyldimethylsilyl
TBDMS-Cl tert-butyldimethylsilyl chloride
TBDPS tert-butyldiphenylsilyl
TEMPO (2,2,6,6-tetramethylpiperidin-1-yl)oxidanyl
tert or t tertiary
TFA trifluoroacetic acid
THF tetrahydrofuran
TIPS triisopropylsilyl
TLC thin layer chromatography
TMS trimethylsilyl or trimethylsilane
TPAP tetrapropylammonium perruthenate
$t_R$ retention time
tBuOH tert-butyl alcohol
v/v volume per volume

EXAMPLES

The compounds presented herein generally can be prepared beginning with commercially available starting materials and using synthetic techniques known to those of skill in the art.

Example 1

2-((3R,5R,6S)-1-(S)-2-(tert-Butylsulfonyl)-1-cyclopropylethyl)-5-(3-chlorophenyl)-6-(4-chlorophenyl)-3-methyl-2-oxopiperidin-3-yl)acetic acid (Example 351 of WO2011/153509 (Amgen Inc.), published Dec. 8, 2011.

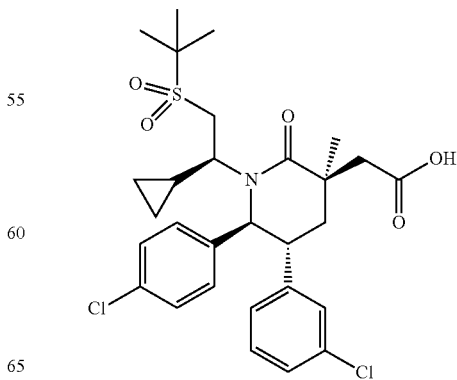

Step A.
2-(3-Chlorophenyl)-1-(4-chlorophenyl)ethanone

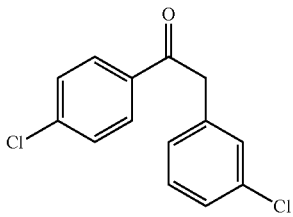 [SMILES: O=C(Cc1cccc(Cl)c1)c1ccc(Cl)cc1]

Sodium bis(trimethylsilyl)amide (1 M in tetrahydrofuran, 117 mL) was slowly added to a −78° C. solution of 2-(3-chlorophenyl) acetic acid (10 g, 58.6 mmol) in tetrahydrofuran (58 mL) over 1 hour. After stirring at −78° C. for 40 minutes, a solution of methyl 4-chlorobenzoate (10 g, 58.6 mmol) in tetrahydrofuran (35 mL) was added over a period of 10 minutes. The reaction was stirred at −78° C. for 3 hours then allowed to warm to 25° C. After two hours at 25° C., the reaction was quenched with saturated aqueous ammonium chloride solution, and most of the tetrahydrofuran was removed under reduced pressure. The residue was extracted with ethyl acetate (2×100 mL). The combined organic layers were washed with saturated sodium chloride solution, dried over sodium sulfate, filtered and the filtrate was concentrated. The product was recrystallized from ether/pentane to provide the title compound as a white solid.

$^1$H NMR (500 MHz, DMSO-$d_6$, δ ppm): 8.05 (m, 2H), 7.62 (m, 2H), 7.33 (m, 3H), 7.21 (br d, J=7.3 Hz, 1H), 4.45 (s, 2H). MS (ESI)=265.1 [M+H]$^+$.

Step B: Methyl 4-(3-chlorophenyl)-5-(4-chlorophenyl)-2-methyl-5-oxopentanoate

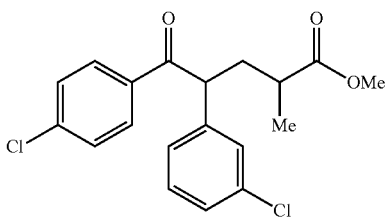 [SMILES: COC(=O)C(C)CC(C(=O)c1ccc(Cl)cc1)c1cccc(Cl)c1]

Methyl methacrylate (12.65 mL, 119 mmol) was added to a solution of 2-(3-chlorophenyl)-1-(4-chlorophenyl)ethanone (30 g, 113 mmol, Example 1, Step A) in tetrahydrofuran (283 mL). Potassium tert-butoxide (1.27 g, 11.3 mmol) was then added and the reaction was stirred at room temperature for 2 days. The solvent was removed under a vacuum and replaced with 300 mL of ethyl acetate. The organic phase was washed with brine (50 mL), water (3×50 mL), and brine (50 mL). The organic phase was dried over magnesium sulfate, filtered and concentrated under a vacuum to afford methyl 4-(3-chlorophenyl)-5-(4-chlorophenyl)-2-methyl-5-oxopentanoate as an approximately 1:1 mixture of diastereomers.

$^1$H NMR (400 MHz, CDCl$_3$, δ ppm): 7.87 (m, 2H), 7.38 (m, 2H), 7.27-7.14 (series of m, 4H), 4.61 (m, 1H), 3.69 (s, 1.5H), 3.60 (s, 1.5; H), 2.45 (m, 1H), 2.34 (m, 1H), 2.10 (ddd, J=13.9, 9.4, 5.5 Hz, 0.5H), 1.96 (ddd, J=13.7, 9.0, 4.3 Hz, 0.5H), 1.22 (d, J=7.0 Hz, 1.5H), 1.16 (d, J=7.0, 1.5; H). MS (ESI)=387.0 [M+23]$^+$.

Step C: (3S,5R,6R)-5-(3-Chlorophenyl)-6-(4-chlorophenyl)-3-methyltetrahydro-2H-pyran-2-one and (3R,5R,6R)-5-(3-chlorophenyl)-6-(4-chlorophenyl)-3-methyltetrahydro-2H-pyran-2-one

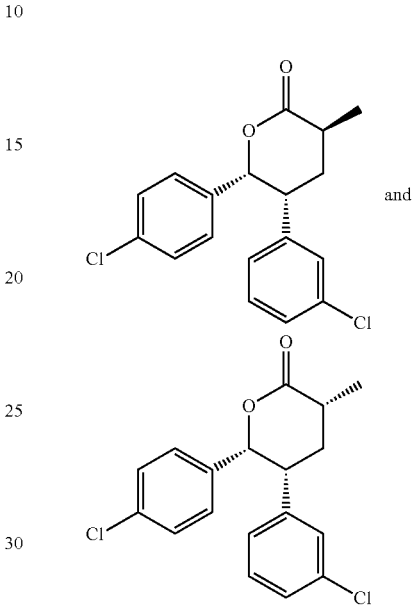

Methyl 4-(3-chlorophenyl)-5-(4-chlorophenyl)-2-methyl-5-oxopentanoate (40 g, 104.0 mmol, Example 1, Step B) was dissolved in 200 mL of anhydrous toluene and concentrated under a vacuum. The residue was placed under high vacuum for 2 hours before use. The compound was split into 2×20 g batches and processed as follows: methyl 4-(3-chlorophenyl)-5-(4-chlorophenyl)-2-methyl-5-oxopentanoate (20 g, 52.0 mmol) in anhydrous 2-propanol (104 mL) was treated with potassium tert-butoxide (2.33 g, 20.8 mmol) in a 250 mL glass hydrogenation vessel. RuCl$_2$(S-xylbinap)(S-DAIPEN) (0.191 g, 0.156 mmol, Strem Chemicals, Inc., Newburyport, Mass.) in 3.8 mL of toluene was added. After 1.5 hours, the vessel was pressurized to 50 psi (344.7 kPa) and purged with hydrogen five times and allowed to stir at room temperature. The reaction was recharged with additional hydrogen as needed. After 3 days, the reactions were combined and partitioned between 50% saturated ammonium chloride solution and ethyl acetate. The aqueous layer was extracted with ethyl acetate. The combined organic phases were washed with brine, dried over magnesium sulfate, filtered, and concentrated. The crude product (predominantly, (4R,5R)-isopropyl 4-(3-chlorophenyl)-5-(4-chlorophenyl)-5-hydroxy-2-methylpentanoate) was dissolved in tetrahydrofuran (450 mL) and methanol (150 mL). Lithium hydroxide (1.4 M, 149 mL, 208 mmol) was added, and the solution was stirred at room temperature for 24 hours. The mixture was concentrated under a vacuum and the residue was redissolved in ethyl acetate. Aqueous 1N hydrochloric acid was added with stirring until the aqueous layer had a pH of about 1. The layers were separated and the organic phase was washed with brine, dried over magnesium sulfate, filtered and concentrated. The material was dissolved in 200 mL of anhydrous toluene and treated with pyridinium p-toluenesulfonate (PPTS, 0.784 g, 3.12 mmol). The reaction was heated to reflux under Dean-Stark conditions until the seco-acid was consumed (about 2 hours). The reaction was cooled to room temperature and washed with saturated sodium bicarbonate (50 mL) and brine (50 mL). The solution was dried over sodium sulfate, filtered and concentrated. The crude material was purified by flash chromatography on silica gel (120 g column; eluting with 100% dichloromethane). The title compounds were obtained as a white solid with an approximate 94:6 enantiomeric.ratio and a 7:3 mixture of methyl diastereomers.

$^1$H NMR (400 MHz, CDCl$_3$, δ ppm): 7.22-6.98 (series of m, 5H), 6.91 (dt, J=7.4, 1.2 Hz, 0.3H), 6.81 (m, 2H), 6.73 (dt, J=7.6, 1.4 Hz, 0.7H), 5.76 (d, J=4.1 Hz, 0.3 H), 5.69 (d, J=4.7 Hz, 0.7H), 3.67 (dt, J=6.6, 4.3 Hz, 0.3H), 3.55 (td, J=7.8, 4.7 Hz, 0.7H), 2.96 (d of quintets, J=13.5, 6.7 Hz, 0.7 H), 2.81 (m, 0.3 H), 2.56 (dt, J=14.3, 8.0 Hz, 0.7; H), 2.32 (dt, J=13.69, 7.0 Hz, 0.3 H), 2.06 (ddd, J=13.7, 8.4, 4.1, 0.3 H), 1.85 (ddd, J=14.1, 12.5, 7.4, 0.7 H), 1.42 (d, J=7.0 Hz, 0.9 H), 1.41 (d, J=6.7 Hz, 2.1H). MS (ESI)=357.0 [M+23]$^+$. [α]$_D$ (22° C., c=1.0, CH$_2$Cl$_2$)=−31.9°; m.p. 98-99° C.

Step D. (3S,5R,6R)-3-Allyl-5-(3-chlorophenyl)-6-(4-chlorophenyl)-3-methyltetrahydro-2H-pyran-2-one

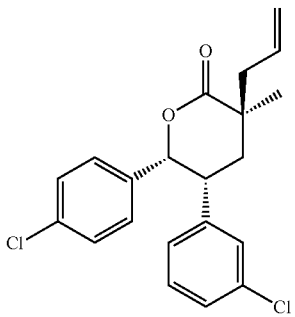 [SMILES: C=CC[C@@]1(C)C[C@H](c2cccc(Cl)c2)[C@H](c2ccc(Cl)cc2)OC1=O]

A solution of (3S,5R,6R)-5-(3-chlorophenyl)-6-(4-chlorophenyl)-3-methyltetrahydro-2H-pyran-2-one and (3R,5S,6S)-5-(3-chlorophenyl)-6-(4-chlorophenyl)-3-methyltetrahydro-2H-pyran-2-one (4.5 g, 13.4 mmol, Example 1, Step C) and allyl bromide (3.48 mL, 40.3 mmol) in tetrahydrofuran (22 mL) at −35° C. (acetonitrile/dry ice bath) was treated with a solution of lithium bis(trimethylsilyl)amide in tetrahydrofuran (1.0 M, 17.45 mL, 17.45 mmol). The reaction was allowed to warm to −5° C. over 1 hour and then was quenched with 50% saturated ammonium chloride. The reaction was diluted with 100 mL of ethyl acetate and the layers were separated. The organic phase was washed with brine, dried over magnesium sulfate, filtered and concentrated under a vacuum to afford the title compound as a white solid upon standing under a vacuum. Chiral SFC (92% CO$_2$, 8% methanol (20 mM ammonia), 5 mL/min, Phenomenex Lux-2 column (Phenomenex, Torrance. CA), 100 bar (10,000 kPa), 40° C., 5 minute method) was used to determine that the compound had an enantiomeric ratio of 96:4. (Major enantiomer: title compound, retention time=2.45 minutes, 96%; minor enantiomer (structure not shown, retention time=2.12 min, 4%). The title compound was recrystallized by adding to heptane (4.7 g slurried in 40 mL) at reflux and 1.5 mL of toluene was added dropwise to solubilize. The solution was cooled to 0° C. The white solid was filtered and rinsed with 20 mL of cold heptanes to afford a white powder. Chiral SFC (92% CO$_2$, 8% methanol, Phenomenex Lux-2 column, same method as above) indicated an enantiomeric ratio of 99.2:0.8. (major enantiomer, 2.45 min, 99.2%; minor enantiomer: 2.12 min, 0.8%)

$^1$H NMR (400 MHz, CDCl$_3$, δ ppm): 7.24 (ddd, J=8.0, 2.0, 1.2 Hz, 1H), 7.20-7.15 (series of m, 3H), 6.91 (t, J=2.0 Hz, 1H), 6.78 (br d, J=7.6 Hz, 1H), 6.60 (m, 2H), 5.84 (ddt, J=17.6, 10.2, 7.4 Hz, 1H), 5.70 (d, J=5.3 Hz, 1H), 5.21-5.13 (series of m, 2H), 3.82 (dt, J=11.7, 4.5 Hz, 1H), 2.62 (ABX J$_{AB}$=13.7 Hz, J$_{AX}$=7.6 Hz, 1H), 2.53 (ABX, J$_{AB}$=13.9 Hz, J$_{BX}$=7.2 Hz, 1H). 1.99 (dd, J=14.1, 11.9 Hz, 1H), 1.92 (ddd, J=13.9, 3.9, 1.2 Hz, 1H). $^{13}$C NMR (CDCl$_3$, 100 MHz, δ ppm): 175.9, 140.2, 134.5, 134.3, 134.0, 132.2, 129.8, 128.6, 128.0, 127.9, 127.8, 126.4, 119.9, 83.9, 44.5, 42.4, 40.7, 31.8, 26.1. MS (ESI)=375.2 [M+H]$^+$. IR=1730 cm$^{-1}$. [α]$_D$. (24° C., c=1.0, CH$_2$Cl$_2$)=−191°. m.p. 111-114° C.

Step E. (2S)-2-((2R)-2-(3-Chlorophenyl)-3-(4-chlorophenyl)-3-hydroxypropyl)-N—((S)-1-cyclopropyl-2-hydroxyethyl)-2-methylpent-4-enamide

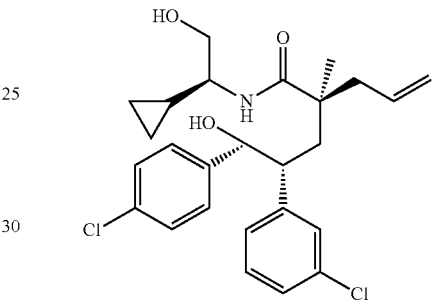

(3S,5R,6R)-3-Allyl-5-(3-chlorophenyl)-6-(4-chlorophenyl)-3-methyltetrahydro-2H-pyran-2-one (125.0 g, 333 mmol, Example 1, Step D) was added to (S)-2-amino-2-cyclopropylethanol (101 g, 999 mmol) and the reaction mixture was heated at 110° C. under argon for 25 hours. The reaction mixture was diluted with isopropyl acetate, cooled to room temperature, and 3 M hydrochloric acid (400 mL) was added slowly. The mixture was stirred at room temperature for 20 minutes, and the layers were separated. The organic layer was washed with 1 M hydrochloric acid (200 mL) and brine, then dried over magnesium sulfate, filtered and concentrated under a vacuum to provide the desired product as a brown oil (159 g).

Step F. (3S,5S,6R,8S)-8-Allyl-6-(3-chlorophenyl)-5-(4-chlorophenyl)-3-cyclopropyl-8-methyl-2,3,5,6,7,8-hexahydrooxazolo[3,2-α]pyridin-4-ium 4-methylbenzenesulfonate

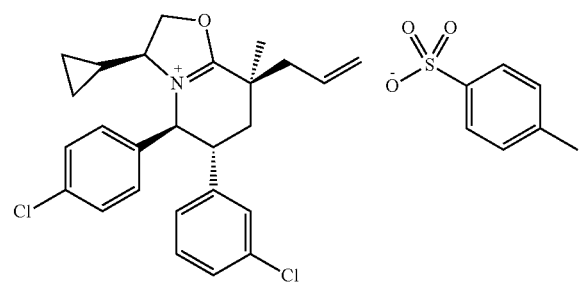

A 2 L 4-necked round-bottomed flask equipped with a magnetic stir bar, addition funnel, septa and internal temperature sensor was charged with p-toluenesulfonic anhydride (240 g, 734 mmol) and anhydrous dichloromethane (600 mL). The internal temperature was adjusted to 14° C. and the mixture was stirred for 10 minutes. A solution of (S)-2-((2R,3R)-2-(3-chlorophenyl)-3-(4-chlorophenyl)-3-hydroxypropyl)-N—((S)-1-cyclopropyl-2-hydroxyethyl)-2-methylpent-4-enamide (159.0 g, 334 mmol, Example 1, Step E) in anhydrous dichloromethane (400 mL) was added to the reaction mixture. The temperature increased to 17° C. before returning to 14° C. The reaction mixture was cooled to 7° C. and 2,6-lutidine (160 mL, 1372 mmol) (dried over activated 4 Å molecular sieves) was added dropwise via addition funnel to the reaction mixture. The addition was complete after 1 hour. The reaction mixture was removed from the water bath and stirred at room temperature for 1 hour. The reaction mixture was heated at reflux for 16 hours. LCMS indicated that some intermediate remained. Additional p-toluenesulfonic anhydride (0.25 equiv) and lutidine (0.5 equiv) were added and the reaction mixture was heated at reflux for 8 hours. LCMS indicated that the reaction was complete. The reaction mixture was cooled to room temperature and added via addition funnel to 1 M aqueous sulfuric acid (764 mL, 764 mmol) with stirring. The addition took 30 minutes, and the solution was stirred at room temperature for 30 minutes thereafter. The layers were separated and the organic layer was dried over magnesium sulfate, filtered and concentrated under a vacuum to provide a brown syrup. To remove any dichloromethane from the syrup it was taken up in ethyl acetate and concentrated under a vacuum twice to provide a thick brown syrup. Ethyl acetate (2 L) was added and the mixture was heated at 60° C. until all of the syrup was dissolved (about 45 minutes). The solution was stirred while cooling to room temperature. Crystals had formed after 2 hours and the mixture was cooled to 10° C. for 1 hour before collecting the solid by vacuum filtration and washing with cold (10° C.) ethyl acetate. This provided 70 g of the desired product as an off-white crystalline solid. The filtrate was concentrated under a vacuum to 1.5 L and the mixture was stirred at 10° C. for 1.5 hours. The mixture was filtered under vacuum to provide a light brown crystalline solid that was shown to be lutidinium tosylate by NMR. The filtrate was concentrated under vacuum to provide a brown syrup (161 g). Heptane was added to the syrup and the mixture was heated. A minimal amount of ethyl acetate was added until the material dissolved. The solution was cooled to room temperature and then placed in the freezer. The resulting solid was collected by vacuum filtration and washed with cold (0° C.) ethyl acetate to provide the desired product as an off-white crystalline solid (34 g). The filtrate was concentrated to provide a dark brown oil and purified by flash chromatography on silica gel (1.5 kg SiO$_2$ column, gradient elution of 20% to 100% acetone in hexanes) to provide the desired product as a light brown syrup (73 g).

$^1$H NMR (500 MHz, CDCl$_3$, δ ppm): −0.3 to −0.2 (m, 2H), 0.06-0.11 (m, 1H), 0.31-0.36 (m, 1H), 0.38-0.43 (m, 1H), 1.57 (s, 3H), 1.91 (dd, J=3.7 and 13.9 Hz, 1H), 2.36 (s, 3H), 2.64 (dd, J=7.3 and 13.7 Hz, 1H), 2.72 (dd, J=7.6 and 13.7 Hz, 1H), 2.95 (t, J=13.9 Hz, 1H), 3.32 (dt, J=3.7 and 10.8 Hz, 1H), 4.47 (t, J=8.6 Hz, 1H), 4.57-4.62 (m, 1H), 5.32 (d, J=16.9 Hz, 1H), 5.35 (d, J=10.3 Hz, 1H), 5.46 (t, J=9.5 Hz, 1H), 5.82 (d, J=10.5 Hz, 1H), 5.84-5.93 (m, 1H), 6.94 (br s, 1H), 7.04 (s, 1H), 7.14-7.20 (m, 5H), 7.28-7.40 (m, 3H), 7.88 (d, J=8.1 Hz, 2H)). MS (ESI) 440.1 [M+H]$^+$.

Step G. (3S,5R,6S)-3-Allyl-1-((S)-2-(tert-butylthio)-1-cyclopropylethyl)-5-(3-chlorophenyl)-6-(4-chlorophenyl)-3-methylpiperidin-2-one

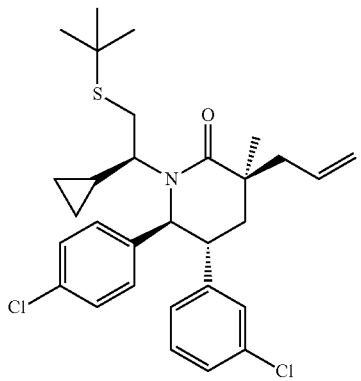 [SMILES: C=CC[C@@]1(C)C[C@H](c2cccc(Cl)c2)[C@@H](c2ccc(Cl)cc2)N([C@H](CSC(C)(C)C)C2CC2)C1=O]

2-Methyl-2-propanethiol (0.195 mL, 1.796 mmol, dried over activated 4 Å molecular sieves) was added to a solution of lithium bis(trimethylsilyl)amide in tetrahydrofuran (1.0 M, 1.8 mL, 1.8 mmol) in anhydrous tetrahydrofuran (4 mL) at room temperature. The reaction mixture was heated at 60° C. After 15 minutes at 60° C., (3S,5S,6R,8S)-8-allyl-6-(3-chlorophenyl)-5-(4-chlorophenyl)-3-cyclopropyl-8-methyl-2,3,5,6,7,8-hexahydrooxazolo[3,2-α]pyridin-4-ium 4-methylbenzenesulfonate (1.00 g, 1.632 mmol, Example 1, Step F) was added as a solid. The reaction mixture was heated at 60° C. for 12 hours and then cooled to room temperature and diluted with water. The solution was extracted with ethyl acetate thrice and the organics were pooled, washed with brine, dried over sodium sulfate, decanted and concentrated under a vacuum to provide a brown oil. Purification by flash chromatography (80 g SiO$_2$ column, gradient elution of 10 to 60% ethyl acetate in hexanes) provided the desired product as a colorless syrup.

$^1$H NMR (500 MHz, CDCl$_3$, δ ppm): −0.88 to −0.85 (m, 1H), −0.16 to −0.13 (m, 1H), 0.22-0.27 (m, 1H), 0.39-0.44 (m, 1H), 1.28 (s, 3H), 1.35 (s, 9H), 1.66-1.71 (m, 1H), 1.86 (dd, J=3.2 and 13.5 Hz, 1H), 2.16 (t, J=13.7, 1H), 2.21-2.27 (m, 1H), 2.60 (dd, J=4.4 and 12.0 Hz, 1H), 2.65 (d, J=7.6 Hz, 2H), 3.12 (dt, J=3.2 and 10.3 Hz, 1H), 3.60 (t, J=11.3 Hz, 1H), 4.68 (d, J=10.3 Hz, 1H), 5.16-5.19 (m, 2H), 5.83-5.92 (m, 1H), 6.79 (d, J=7.6 Hz, 1H), 6.93-7.04 (m, 3H), 7.09-7.16 (m, 2H), 7.19-7.24 (m, 2H). MS (ESI) 530.2 [M+H]$^+$.

Step H. 2-((3R,5R,6S)-1-((S)-2-(tert-Butylsulfonyl)-1-cyclopropylethyl)-5-(3-chlorophenyl)-6-(4-chlorophenyl)-3-methyl-2-oxopiperidin-3-yl)acetic acid

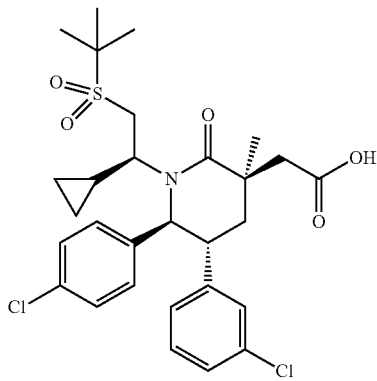 [SMILES: CC(C)(C)S(=O)(=O)C[C@H](C1CC1)N1C(=O)[C@@](C)(CC(=O)O)C[C@H](c2cccc(Cl)c2)[C@H]1c1ccc(Cl)cc1]

Ruthenium(III) chloride hydrate (30.0 mg, 0.135 mmol) was added to a solution of (3S,5R,6S)-3-allyl-1-((S)-2-(tert-butylthio)-1-cyclopropylethyl)-5-(3-chlorophenyl)-6-(4-chlorophenyl)-3-methylpiperidin-2-one (3.25 g, 6.13 mmol, Example 1, Step H) and sodium periodate (1.33 g) in ethyl acetate (12 mL), acetonitrile (12 mL) and water (18 mL) at 18° C. The temperature rose to 25° C. upon addition. Additional sodium periodate was added in five 1.33 g portions over 30 minutes while maintaining the temperature below 22° C. LCMS after 1.5 hours indicated that the reaction was incomplete, and sodium periodate (1 equivalent) was added. After 1.5 hours the reaction mixture was vacuum filtered, washed with ethyl acetate, and the layers were separated. The aqueous layer was extracted with ethyl acetate and the organics were combined, washed with brine, dried over magnesium sulfate, filtered and concentrated under a vacuum to provide a green oil. Purification by flash chromatography (330 g SiO$_2$ column, gradient elution of 0% to 20% isopropanol in hexanes provided the title compound as a white solid.

$^1$H NMR (500 MHz, CDCl$_3$, δ ppm): −1.15 to −1.05 (m, 1H), −0.35 to −0.25 (m, 1H), 0.18-0.28 (m, 1H), 0.33-0.40 (m, 1H), 1.45 (s, 9H), 1.51 (s, 3H), 1.86 (dd, J=2.7 and 13.7 Hz, 1H), 1.87-1.93 (m, 1H), 2.47 (t, J=13.9, 1H), 2.72-2.76 (m, 1H), 2.76 (d, J=15.5 Hz, 1H), 2.93 (d, J=13.7 Hz, 1H), 3.12 (d, J=15.1 Hz, 1H), 3.12 (dt, J=2.7 and 12.5 Hz, 1H), 4.29 (t, J=11.5 Hz, 1H), 4.95 (d, J=10.8 Hz, 1H), 6.86-6.89 (m, 1H), 6.96 (br s, 1H), 7.08-7.14 (m, 3H), 7.15-7.35 (m, 3H). MS (ESI) 580.2 [M+H]$^+$.

Example 2

2-((3R,5R,6S)-1-((S)-2-(tert-Butylsulfonyl)-1-cyclopropylethyl)-5-(3-chlorophenyl)-6-(4-chlorophenyl)-3-methyl-2-oxopiperidin-3-yl)acetamide

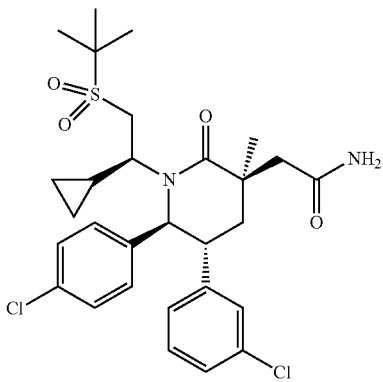 [SMILES: CC(C)(C)S(=O)(=O)C[C@H](C1CC1)N1C(=O)[C@@](C)(CC(N)=O)C[C@H](c2cccc(Cl)c2)[C@H]1c1ccc(Cl)cc1]

Oxalyl chloride (0.033 mL, 0.379 mmol) was added to a solution of 2-((3R,5R,6S)-1-((S)-2-(tert-butylsulfonyl)-1-cyclopropylethyl)-5-(3-chlorophenyl)-6-(4-chlorophenyl)-3-methyl-2-oxopiperidin-3-yl)acetic acid (0.200 g, 0.344 mmol, Example 1, Step H) in anhydrous dichloromethane (1.5 mL) at room temperature. The reaction mixture was stirred at room temperature for 1 hour and then concentrated under a vacuum to provide the acid chloride as a white foam (206 mg). Lithium bis(trimethylsilyl)amide (1.0 M in tetrahydrofuran, 0.516 mL, 0.516 mmol) and anhydrous tetrahydrofuran (0.5 mL) were added at room temperature. The reaction mixture was stirred at room temperature for 5.5 hours and was then diluted with 1 N hydrochloric acid and extracted with ethyl acetate thrice. The organics were pooled, washed with brine, dried over sodium sulfate, decanted and concentrated under a vacuum to provide a yellow foam. Purification by flash chromatography (12 g SiO$_2$ column; gradient elution of 35% to 100% ethyl acetate) provided the title compound as an off-white foam.

$^1$H NMR (500 MHz, CDCl$_3$, δ ppm): −1.10 to −1.00 (m, 1H), −0.38 to −0.325 (m, 1H), 0.17-0.26 (m, 1H), 0.30-0.38 (m, 1H), 1.43 (s, 3H), 1.44 (s, 9H), 1.85-1.92 (m, 1H), 2.00 (dd, J=2.7 and 13.5 Hz, 1H), 2.39 (t, J=13.7, 1H), 2.65-2.75 (m, 1H), 2.73-2.80 (m, 2H), 2.90-2.96 (m, 1H), 3.31 (dt, J=2.9 and 10.8 Hz, 1H), 4.30-4.38 (m, 1H), 4.96 (d, J=10.8 Hz, 1H), 5.63 (br s, 1H), 6.64 (br s, 1H), 6.90-6.91 (m, 1H), 7.00 (s, 2H), 7.06-7.11 (m, 3H), 7.12-7.29 (m, 2H). MS (ESI) 579.2 [M+H]$^+$.

Example 3

2-((3R,5R,6S)-1-((S)-2-(tert-Butylsulfonyl)-1-cyclopropylethyl)-5-(3-chlorophenyl)-6-(4-chlorophenyl)-3-methyl-2-oxopiperidin-3-yl)-N-phenylacetamide

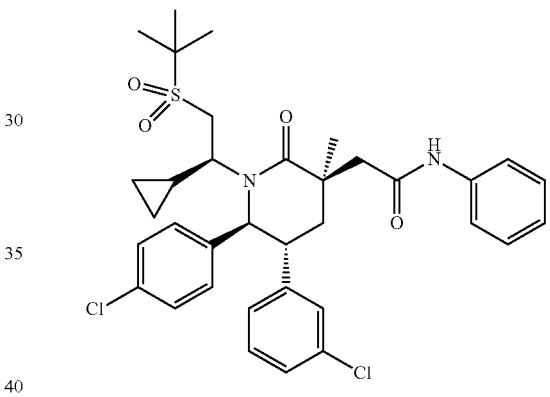

N-(3-Dimethylaminopropyl)-N'-ethylcarbodiimide hydrochloride (EDC, 0.117 g, 0.612 mmol) was added to a solution of 2-((3R,5R,6S)-1-((S)-2-(tert-butylsulfonyl)-1-cyclopropylethyl)-5-(3-chlorophenyl)-6-(4-chlorophenyl)-3-methyl-2-oxopiperidin-3-yl)acetic acid (0.118 g, 0.204 mmol, Example 1, Step H) and aniline (0.020 mL, 0.225 mmol) at 0° C. After the addition was complete, the reaction mixture was removed from the ice bath and stirred at room temperature for 19 hours. The reaction mixture was diluted with ice-cold 1 M hydrochloric acid to adjust the pH to 1 and the solution was extracted twice with ether. The combined organic layer was washed with brine, dried over sodium sulfate, decanted and concentrated under a vacuum to provide an orange oil. Purification by flash chromatography (12 g SiO$_2$ column, gradient elution of 15% to 100% ethyl acetate in hexanes provided the title compound as a white foam.

$^1$H NMR (500 MHz, CDCl$_3$, δ ppm): −1.32 to −1.20 (m, 1H), −0.40 to −0.28 (m, 1H), −0.28 to −0.10 (m, 1H), 0.30-0.40 (m, 1H), 1.45 (s, 9H), 1.47 (s, 3H), 1.94 (br s, 1H), 2.07 (dd, J=2.7 and 13.7 Hz, 1H), 2.39 (t, J=13.7, 1H), 2.67-2.73 (m, 2H), 2.95 (t, J=13.5 Hz, 2H), 3.30 (dt, J=2.7 and 11.0 Hz, 1H), 4.31 (br t, J=11.7 Hz, 1H), 4.94 (d, J=10.8 Hz, 1H), 6.86-6.89 (m, 1H), 6.99 (s, 1H), 7.02-7.09 (m, 6H), 7.17 (t, J=7.3 Hz, 1H), 7.38 (t, J=8.3 Hz, 2H), 7.66 (d, J=7.8 Hz, 2H). MS (ESI) 655.3 [M+H]$^+$.

Example 4

2-((3R,5R,6S)-1-((S)-2-(tert-Butylsulfonyl)-1-cyclopropylethyl)-6-(4-chloro-3-fluorophenyl)-5-(3-chlorophenyl)-3-methyl-2-oxopiperidin-3-yl)acetic acid

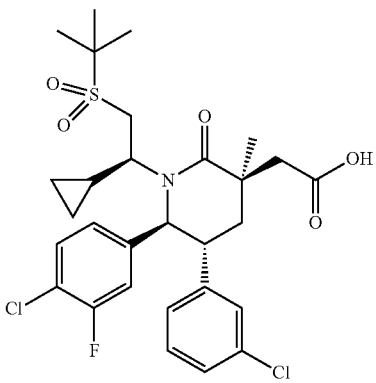 [SMILES: CC(C)(C)S(=O)(=O)C[C@H](C1CC1)N1C(=O)[C@@](C)(CC(=O)O)C[C@H](c2cccc(Cl)c2)[C@H]1c1ccc(Cl)c(F)c1]

Step A. Methyl-4-chloro-3-fluorobenzoate

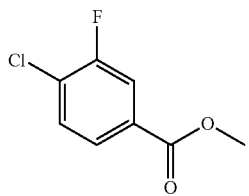

A solution of 4-chloro-3-fluoro benzoic acid (450.0 g, 2.586 mol, Fluororochem, Derbyshire, UK) in methanol (4.5 L) was cooled to 0° C. and thionyl chloride (450.0 mL) was added over 30 minutes. The reaction mixture was stirred for 12 hours at ambient temperature. The reaction was monitored by TLC. Upon completion, the solvent was removed under reduced pressure and the residue was quenched with 1.0 M sodium bicarbonate solution (500 mL). The aqueous layer was extracted with dichloromethane (2×5.0 L). The combined organic layer was washed with brine (2.5 L), dried over anhydrous sodium sulfate and concentrated under reduced pressure afforded the title compound as light brown solid. The crude compound was used in the next step without further purification.

$^1$H NMR (400 MHz, CDCl$_3$, δ ppm): 7.82-7.74 (m, 2H), 7.46 (dd, J=8.2, 7.5 Hz, 1H), 3.92 (s, 3H).

Step B. 1-(4-chloro-3-fluorophenyl)-2-(3-chlorophenyl)ethanone

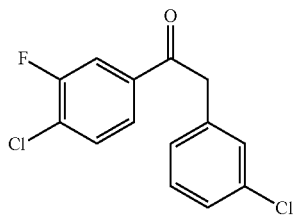 [SMILES: O=C(Cc1cccc(Cl)c1)c1ccc(Cl)c(F)c1]

Sodium bis(trimethylsilyl)amide (1 M in tetrahydrofuran, 4 L, 4000 mmol) was added over 1 hour to a solution of 3-chlorophenyl acetic acid (250.0 g, 1465 mmol) in anhydrous tetrahydrofuran (1.75 L) at −78° C. under nitrogen. The resulting reaction mixture was stirred for an additional hour at −78° C. Then, a solution of methyl-4-chloro-3-fluorobenzoate (221.0 g, 1175 mmol, Example 4, Step A) in tetrahydrofuran (500 mL) was added over 1 hour at −78° C., and the resulting reaction mixture was stirred at the same temperature for 2 hours. The reaction was monitored by TLC. On completion, reaction mixture was quenched with 2 N hydrochloric acid (2.5 L) and aqueous phase was extracted with ethyl acetate (2×2.5 L). The combined organic layer was washed with brine (2.5 L), dried over anhydrous sodium sulfate and concentrated under reduced pressure to provide the crude material which was purified by flash column chromatography (silica gel: 100 to 200 mesh, product eluted in 2% ethyl acetate in hexane) to afford the title compound as a white solid.

$^1$H NMR (400 MHz, CDCl$_3$, δ ppm): 7.74 (ddd, J=10.1, 8.9, 1.8 Hz, 2H), 7.56-7.48 (m, 1H), 7.26 (t, J=6.4 Hz, 3H), 7.12 (d, J=5.7 Hz, 1H), 4.22 (s, 2H). MS (ESI) 282.9 [M+H]$^+$.

Step C. Methyl 5-(4-chloro-3-fluorophenyl)-4-(3-chlorophenyl)-2-methyl-5-oxopentanoate

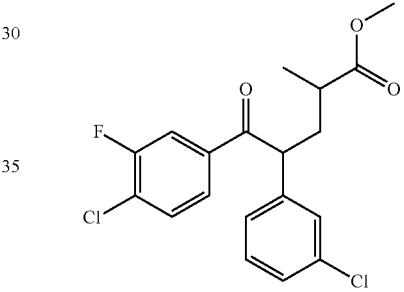

Methyl methacrylate (125.0 g, 1097 mmol) and potassium tert-butoxide (1 M in tetrahydrofuran, 115 mL, 115 mmol) were sequentially added to a solution of 1-(4-chloro-3-fluorophenyl)-2-(3-chlorophenyl)ethanone (327.0 g, 1160 mmol, Example 4, Step B) in anhydrous tetrahydrofuran (2.61 L), at 0° C. The reaction mixture was stirred for 1 hour at 0° C. and then warmed to ambient temperature and stirred for 12 hours. On completion, the reaction was quenched with water (1.0 L) and extracted with ethyl acetate (2×2.5 L). The combined organic layer was washed with brine, dried over anhydrous sodium sulfate and concentrated under reduced pressure to get the crude material which was purified by flash column chromatography (silica gel: 60 to 120 mesh, product eluted in 4% ethyl acetate in hexane) affording the title compound (mixture of diastereomers) as light yellow liquid.

$^1$H NMR (400 MHz, CDCl$_3$, δ ppm): 7.74-7.61 (m, 4H), 7.47-7.40 (m, 2H), 7.28-7.18 (m, 6H), 7.16-7.10 (m, 2H), 4.56 (m, 2H), 3.68 (s, 3H), 3.60 (s, 3H), 2.50-2.39 (m, 2H), 2.37-2.25 (m, 2H), 2.10-2.02 (m, 1H), 1.94 (ddd, J=13.6, 9.1, 4.2 Hz, 1H), 1.21 (d, J=7.0 Hz, 3H), 1.15 (d, J=7.0 Hz, 3H). MS (ESI) 383.0 [M+H]$^+$.

Step D. (3S,5R,6R)-6-(4-Chloro-3-fluorophenyl)-5-(3-chlorophenyl)-3-methyltetrahydro-2H-pyran-2-one and (3R,5R,6R)-6-(4-chloro-3-fluorophenyl)-5-(3-chlorophenyl)-3-methyltetrahydro-2H-pyran-2-one

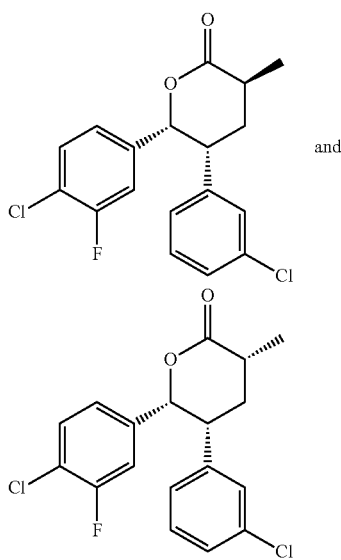

and

In a 2000 mL reaction vessel charged with methyl 5-(4-chloro-3-fluorophenyl)-4-(3-chlorophenyl)-2-methyl-5-oxopentanoate (138.0 g, 360 mmol, Example 4, Step C) (which was cooled on ice for 10 minutes before transferring to a glove bag) anhydrous 2-propanol (500 mL), and potassium tert-butoxide (16.16 g, 144 mmol) were sequentially added while in a sealed glove bag under argon. This mixture was allowed to stir for 30 minutes. RuCl$_2$(S-xylbinap)(S-DAIPEN) (1.759 g, 1.440 mmol, Strem Chemicals, Inc., Newburyport, Mass., weighed in the glove bag) in 30.0 mL toluene was added. The reaction was vigorously stirred at room temperature for 2 hours. The vessel was set on a hydrogenation apparatus, purged with hydrogen 3 times and pressurized to 50 psi (344.7 kPa). The reaction was allowed to stir overnight at room temperature. On completion, the reaction was quenched with water (1.5 L) and extracted with ethyl acetate (2×2.5 L). The organic layer was washed with brine (1.5 L), dried over anhydrous sodium sulfate and concentrated under reduced pressure to get crude material which was purified by flash column chromatography (silica gel; 60-120 mesh; product eluted in 12% ethyl acetate in hexane) to provide a dark colored liquid as a mixture of diastereomers.

The product was dissolved in (240.0 g, 581 mmol) in tetrahydrofuran (1.9 L) and methanol (480 mL), and lithium hydroxide monohydrate (2.5 M aqueous solution, 480.0 mL) was added. The reaction mixture was stirred at ambient temperature for 12 hours. On completion, the solvent was removed under reduced pressure and the residue was acidified with 2 N hydrochloric acid to a pH between 5 and 6. The aqueous phase was extracted with ethyl acetate (2×1.0 L). The combined organic layer was washed with brine (750 mL), dried over anhydrous sodium sulfate, filtered, and concentrated under reduced pressure to provide a dark colored liquid, which was used without further purification.

A portion of the crude intermediate (25.4 g, predominantly seco acid) was added to a 500 mL round bottom flask, equipped with a Dean-Stark apparatus. Pyridinium p-toluenesulfonate (0.516 g, 2.053 mmol) and toluene (274 mL) were added, and the mixture was refluxed for 1 hour (oil bath temperature about 150° C.). The reaction was cooled to room temperature and concentrated under reduced pressure. The reaction was diluted with saturated aqueous sodium bicarbonate (150 mL), extracted with diethyl ether (2×150 mL), and washed with brine (150 mL). The combined organic layer was dried over magnesium sulfate, filtered and concentrated under reduced pressure. Purification by flash column chromatography (divided into 3 portions, 330 g SiO$_2$/each, gradient elution of 0% to 30% acetone in hexanes, 35 minutes) provided the title compounds as a pale yellow solid and a 1:1.6 mixture of diastereomers at C2. MS (ESI) 353.05 [M+H]$^+$.

Step E. (3S,5R,6R)-3-Allyl-6-(4-chloro-3-fluorophenyl)-5-(3-chlorophenyl)-3-methyltetrahydro-2H-pyran-2-one

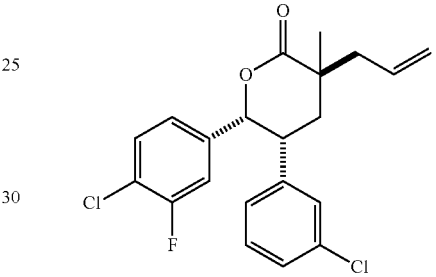

(3S,5R,6R)-6-(4-Chloro-3-fluorophenyl)-5-(3-chlorophenyl)-3-methyltetrahydro-2H-pyran-2-one and (3R,5R,6R)-6-(4-chloro-3-fluorophenyl)-5-(3-chlorophenyl)-3-methyltetrahydro-2H-pyran-2-one (18 g, 51.0 mmol, Example 4, Step D) was added to an oven dried 500 mL round-bottom flask. The solid was dissolved in anhydrous toluene and concentrated to remove adventitious water. 3-Bromoprop-1-ene (11.02 mL, 127 mmol, passed neat through basic alumina prior to addition) in tetrahydrofuran (200 mL) was added and the reaction vessel was evacuated and refilled with argon three times. Lithium bis(trimethylsilyl)amide (1.0 M, 56.1 mL, 56.1 mmol) was added dropwise at −40° C. (dry ice/acetonitrile bath) and stirred under argon. The reaction was allowed to gradually warm to −10° C. and stirred at −10° C. for 3 hours. The reaction was quenched with saturated ammonium chloride (10 mL), concentrated, and the crude product was diluted in water (150 mL) and diethyl ether (200 mL). The layers were separated and the aqueous layer was washed twice more with diethyl ether (200 mL/each). The combined organic layer was washed with brine (100 mL), dried over magnesium sulfate, filtered, and concentrated under reduced pressure to a residue. The residue was purified by flash chromatography (2×330 g silica gel columns, gradient elution of 0% to 30% acetone in hexanes) to provide the title compound as a white solid. The product can alternatively be crystallized from a minimum of hexanes in dichloromethane. Enantiomeric excess was determined to be 87% by chiral SFC (90% CO$_2$, 10% methanol (20 mM ammonia), 5.0 mL/min, 100 bar (10,000 kPa), 40° C., 5 minute method, Phenomenex Lux-2 (Phenomenex, Torrance, Calif.) (100 mm×4.6 mm, 5 µm column), retention times: 1.62 min. (minor) and 2.17 min. (major)). The purity could be upgraded to >98% through recrystallization in hexanes and dichloromethane.

¹H NMR (400 MHz, CDCl₃, δ ppm): 7.24-7.17 (m, 3H), 6.94 (s, 1H), 6.80 (d, J=7.5 Hz, 1H), 6.48 (dd, J=10.0, 1.9 Hz, 1H), 6.40 (d, J=8.3 Hz, 1H), 5.90-5.76 (m, 1H), 5.69 (d, J=5.2 Hz, 1H), 5.20-5.13 (m, 2H), 3.81 (dd, J=13.9, 6.9 Hz, 1H), 2.62 (dd, J=13.8, 7.6 Hz, 1H), 2.50 (dd, J=13.8, 7.3 Hz, 1H), 1.96 (d, J=8.4 Hz, 2H), 1.40 (s, 3H). MS (ESI) 393.1 [M+H]⁺.

Step F. (2S)-2-((2R)-3-(4-Chloro-3-fluorophenyl)-2-(3-chlorophenyl)-3-hydroxypropyl)-N—((S)-1-cyclopropyl-2-hydroxyethyl)-2-methylpent-4-enamide

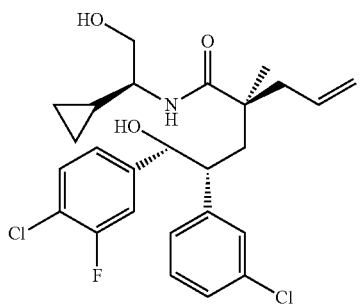 [SMILES: C=CC[C@@](C)(C[C@H](c1cccc(Cl)c1)[C@H](O)c1ccc(Cl)c(F)c1)C(=O)N[C@H](CO)C1CC1]

Sodium methoxide (25% in methanol, 60.7 ml, 265 mmol) was added to a solution of (S)-2-amino-2-cyclopropylethanol hydrochloride (36.5 g, 265 mmol, NetChem Inc., Ontario, Canada) in methanol (177 mL) at 0° C. A precipitate formed during the addition. After the addition was complete, the reaction mixture was removed from the ice bath and warmed to room temperature. The reaction mixture was filtered under a vacuum and the solid was washed with dichloromethane. The filtrate was concentrated under a vacuum to provide a cloudy brown oil. The oil was taken up in dichloromethane (150 mL), filtered under a vacuum and the solid phase washed with dichloromethane to provide the filtrate as a clear orange solution. The solution was concentrated under a vacuum to provide (S)-2-amino-2-cyclopropylethanol as a light brown liquid.

(3S,5R,6R)-3-Allyl-6-(4-chloro-3-fluorophenyl)-5-(3-chlorophenyl)-3-methyltetrahydro-2H-pyran-2-one (32 g, 81 mmol, Example 4, Step E) was combined with (S)-2-amino-2-cyclopropylethanol (26.7 g, 265 mmol) and the suspension was heated at 100° C. overnight. The reaction mixture was cooled to room temperature, diluted with ethyl acetate and washed with 1 N hydrochloric acid (2×), water, and brine. The organic layer was dried over magnesium sulfate and concentrated under vacuum to provide the title compound as a white solid.

¹H NMR (500 MHz, CDCl₃, δ ppm): 0.23-0.30 (m, 2H), 0.45-0.56 (m, 2H), 0.81 (m, 1H), 1.12 (s, 3H), 1.92-2.09 (m, 3H), 2.39 (dd, J=13.6, 7.2 Hz, 1H), 2.86 (br s, 1H), 2.95 (dtd, J=9.5, 6.3, 6.3, 2.9 Hz, 1H), 3.44 (dd, J=11.0, 5.6 Hz, 1H), 3.49 (m, 1H), 3.61 (dd, J=11.0, 2.9 Hz, 1H), 4.78 (d, J=5.6 Hz, 1H), 4.95-5.13 (m, 2H), 5.63 (m, 1H), 5.99 (d, J=6.4 Hz, 1H), 6.94-7.16 (m, 3H), 7.16-7.32 (m, 4H). MS (ESI) 494 [M+H]⁺.

Step G. (3S,5R,6S)-3-Allyl-6-(4-chloro-3-fluorophenyl)-5-(3-chlorophenyl)-1-((S)-1-cyclopropyl-2-hydroxyethyl)-3-methylpiperidin-2-one

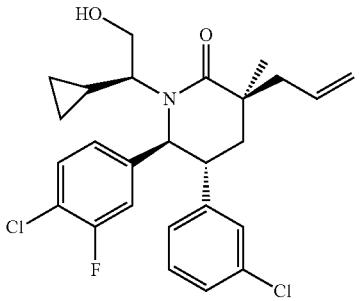 [SMILES: C=CC[C@@]1(C)C[C@H](c2cccc(Cl)c2)[C@@H](c2ccc(Cl)c(F)c2)N([C@H](CO)C2CC2)C1=O]

A solution of (2S)-2-((2R)-3-(4-chloro-3-fluorophenyl)-2-(3-chlorophenyl)-3-hydroxypropyl)-N—((S)-1-cyclopropyl-2-hydroxyethyl)-2-methylpent-4-enamide (40.2 g, 81 mmol, Example 4, Step F) in dichloromethane (80 mL) was added p-toluenesulfonic anhydride (66.3 g, 203 mmol) in dichloromethane (220 mL) at 0° C., and the reaction mixture was stirred for 10 minutes at same the temperature. 2,6-Lutidine (43.6 mL, 374 mmol, Aldrich, St. Louis, Mo.) was added dropwise via addition funnel at 0° C. The reaction mixture was slowly warmed to room temperature, and then it was stirred at reflux. After 24 hours, sodium bicarbonate (68.3 g, 814 mmol) in water (600 mL) and 1,2-dichloroethane (300 mL) were added in succession. The reaction mixture was heated at reflux for an hour and then cooled to room temperature. The layers were separated and the aqueous layer was extracted with dichloromethane. The combined organic layer was washed with 1 N hydrochloric acid, water, and brine, then concentrated under reduced pressure. The residue was purified by flash chromatography (1.5 kg SiO₂ column, gradient elution of 10% to 50% ethyl acetate in hexanes) to provide the title compound as a white solid.

¹H NMR (500 MHz, CDCl₃, δ ppm): 0.06 (m, 1H), 0.26 (m, 1H), 0.57-0.67 (m, 2H), 0.85 (m, 1H), 1.25 (s, 3H), 1.85-2.20 (m, 2H), 2.57-2.65 (m, 2H), 3.09 (ddd, J=11.8, 9.8, 4.8 Hz, 1H), 3.19 (t, J=10.0 Hz, 1H), 3.36 (td, J=10.3, 4.6 Hz, 1H), 3.63 (dd, J=11.0, 4.6 Hz, 1H), 4.86 (d, J=10.0 Hz, 1H), 5.16-5.19 (m, 2H), 5.87 (m, 1H), 6.77 (dd, J=7.7, 1.6 Hz, 1H), 6.80-6.90 (m, 2H), 7.02 (t, J=2.0 Hz, 1H), 7.16 (dd, J=10.0, 7.7 Hz, 1H), 7.21 (dd, J=10.0, 1.6 Hz, 1H), 7.29 (t, J=10.0 Hz, 1H). MS (ESI) 476 [M+H]⁺.

Step H. (3S,5S,6R,8S)-8-Allyl-5-(4-chloro-3-fluorophenyl)-6-(3-chlorophenyl)-3-cyclopropyl-8-methyl-2,3,5,6,7,8-hexahydrooxazolo[3,2-α]pyridin-4-ium 4-methylbenzenesulfonate

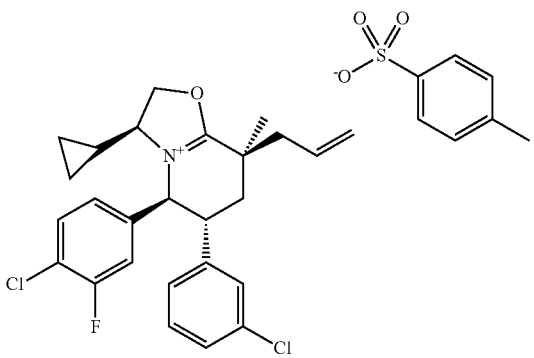

p-Toluenesulfonic acid monohydrate (30.3 g, 159 mmol, Aldrich, St. Louis, Mo.) was added to a solution of (3S,5R, 6S)-3-allyl-6-(4-chloro-3-fluorophenyl)-5-(3-chlorophenyl)-1-((S)-1-cyclopropyl-2-hydroxyethyl)-3-methylpiperidin-2-one (73.6 g, 154 mmol) in toluene (386 mL). The reaction mixture was heated at reflux using a Dean-Stark apparatus. After 4 hours, the reaction was cooled and concentrated under reduced pressure to provide the title compound as a pale yellow syrup. The crude product was used in next step without further purification.

$^1$H NMR (500 MHz, CDCl$_3$, δ ppm): −0.25 to −0.10 (m, 2H), 0.08-0.18 (m, 1H), 0.33-0.50 (m, 2H), 1.57 (s, 3H), 1.92 (dd, J=3.7 and 13.9 Hz, 1H), 2.37 (s, 3H), 2.63 (dd, J=7.3 and 13.7 Hz, 1H), 2.72 (dd, J=7.6 and 13.7 Hz, 1H), 2.93 (t, J=13.7 Hz, 1H), 3.29 (m, 1H), 4.51 (t, J=8.6 Hz, 1H), 4.57-4.63 (m, 1H), 5.33 (d, J=17.1 Hz, 1H), 5.37 (d, J=10.5 Hz, 1H), 5.47 (dd, J=9.1 and 10.0 Hz, 1H), 5.75-5.93 (m, 2H), 6.80 (br s, 1H), 7.08 (s, 1H), 7.16-7.20 (m, 5H), 7.25-7.32 (m, 2H), 7.87 (d, J=8.3 Hz, 2H). MS (ESI) 458 [M+H]$^+$.

Step I. (3S,5R,6S)-3-Allyl-1-((S)-2-(tert-butylthio)-1-cyclopropylethyl)-6-(4-chloro-3-fluorophenyl)-5-(3-chlorophenyl)-3-methylpiperidin-2-one

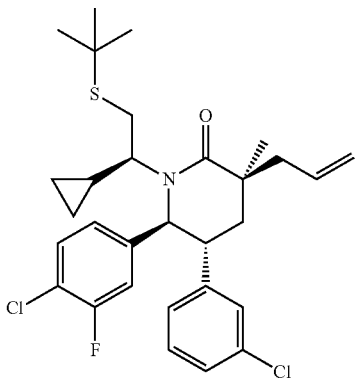 [SMILES: C=CC[C@@]1(C)C[C@H](c2cccc(Cl)c2)[C@@H](c2ccc(Cl)c(F)c2)N([C@H](CSC(C)(C)C)C2CC2)C1=O]

2-Methyl-2-propanethiol (15.25 mL, 135 mmol, dried over activated 4 Å molecular sieves) was added to a solution of lithium bis(trimethylsilyl)amide in tetrahydrofuran (1.0 M, 135 mL, 135 mmol) at room temperature under argon in a 500 mL round-bottomed flask. The reaction mixture was heated to 60° C. After 30 minutes, a solution of (3S,5S,6R,8S)-8-allyl-5-(4-chloro-3-fluorophenyl)-6-(3-chlorophenyl)-3-cyclopropyl-8-methyl-2,3,5,6,7,8-hexahydrooxazolo[3,2-60 ]pyridin-4-ium 4-methylbenzenesulfonate (78 g, 123 mmol, Example 4, Step H) in anhydrous tetrahydrofuran (100 mL) was added via cannula. The reaction mixture was heated at 60° C. for 3 hours and then cooled to room temperature. The reaction mixture was quenched with water and extracted thrice with ethyl acetate. The organics were pooled, washed with brine, dried over magnesium sulfate, filtered and concentrated under a vacuum to provide a yellow foam. Purification by flash column chromatography (1.5 kg SiO$_2$ column, gradient elution with 5% to 30% ethyl acetate in hexanes provided the title compound as an off-white foam.

$^1$H NMR (400 MHz, CDCl$_3$, δ ppm): −0.89 to −0.80 (m, 1H), −0.15 to −0.09 (m, 1H), 0.27-0.34 (m, 1H), 0.41-0.48 (m, 1H), 1.28 (s, 3H), 1.35 (s, 9H), 1.70-1.77 (m, 1H), 1.86 (dd, J=3.1 and 13.5 Hz, 1H), 2.16 (t, J=13.7, 1H), 2.17-2.23 (m, 1H), 2.60-2.63 (m, 3H), 3.09 (dt, J=3.1 and 10.4 Hz, 1H), 3.62 (t, J=11.1 Hz, 1H), 4.70 (d, J=10.1 Hz, 1H), 5.16 (s, 1H), 5.19-5.21 (m, 1H), 5.82-5.93 (m, 1H), 6.65-6.80 (m, 1H), 6.80-6.83 (m, 1H), 6.84-6.98 (m, 1H), 7.05-7.07 (m, 1H), 7.12-7.18 (m, 2H), 7.19-7.26 (m, 1H). MS (ESI) 548.2 [M+H]$^+$.

Step J. 2-((3R,5R,6S)-1-((S)-2-(tert-Butylsulfonyl)-1-cyclopropylethyl)-6-(4-chloro-3-fluorophenyl)-5-(3-chlorophenyl)-3-methyl-2-oxopiperidin-3-yl)acetic acid

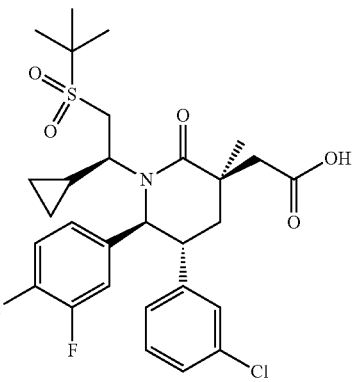

Ruthenium(III) chloride hydrate (0.562 mg, 2.493 mmol) was added to a mixture of (3S,5R,6S)-3-allyl-1-((S)-2-(tert-butylthio)-1-cyclopropylethyl)-6-(4-chloro-3-fluorophenyl)-5-(3-chlorophenyl)-3-methylpiperidin-2-one (62.17 g, 113 mmol, Example 4, Step I) and sodium periodate (24.67 g) in ethyl acetate (216 mL), acetonitrile (216 mL) and water (324 mL) at 20° C. The temperature quickly rose to 29° C. The reaction mixture was cooled to 20° C. and the remaining equivalents of sodium periodate were added in five 24.67 g portions over 2 hours, being careful to maintain an internal reaction temperature below 25° C. The reaction was incomplete, so additional sodium periodate (13 g) was added. The temperature increased from 22° C. to 25° C. After stirring for an additional 1.5 hours, the reaction mixture was filtered under a vacuum and washed with ethyl acetate. The layers were separated and the aqueous layer was extracted with ethyl acetate. The organics were pooled, washed with brine, dried over magnesium sulfate, filtered and concentrated under a vacuum to provide a dark green foam. Purification by flash column chromatography (1.5 kg SiO$_2$ column, gradient elution of 0% to 20% isopropanol in hexanes) provided an off-white foam. 15% Ethyl acetate in heptanes (970 mL) was added to the foam, and the mixture was heated at 80° C. until the foam dissolved. The solution was then cooled slowly, and at 60° C. the solution was seeded with previously obtained crystalline material. The mixture was cooled to room temperature and then allowed to stand at room temperature for 2 hours before collecting the solid by vacuum filtration to provide a white solid with a very pale pink hue (57.1 g). The mother liquor was concentrated under a vacuum to provide a pink foam (8.7 g). 15% ethyl acetate in heptanes (130 mL) was added to the foam, and it was heated at 80° C. to completely dissolve the material. The solution was cooled, and at 50° C., it was seeded with crystalline material. After cooling to room temperature the solid was collected by vacuum filtration to provide a white crystalline solid with a very pale pink hue.

$^1$H NMR (500 MHz, CDCl$_3$, δ ppm): −1.10 to −1.00 (m, 1H), −0.30 to −0.22 (m, 1H), 0.27-0.37 (m, 1H), 0.38-0.43

(m, 1H), 1.45 (s, 9H), 1.50 (s, 3H), 1.87 (dd, J=2.7 and 13.7 Hz, 1H), 1.89-1.95 (m, 1H), 2.46 (t, J=13.7, 1H), 2.69-2.73 (m, 1H), 2.78 (d, J=14.9 Hz, 1H), 2.93 (dd, J=2.0 and 13.7 Hz, 1H), 3.07 (d, J=14.9 Hz, 1H), 3.11 (dt, J=2.7 and 11.0 Hz, 1H), 4.30 (t, J=13.5 Hz, 1H), 4.98 (d, J=10.8 Hz, 1H), 6.75-6.87 (m, 1H), 6.88-6.90 (m, 1H), 6.98 (br s, 1H), 7.02-7.09 (m, 1H), 7.11-7.16 (m, 2H), 7.16-7.25 (m, 1H). MS (ESI) 598.1 [M+H]$^+$.

Example 5

4-(2-((3R,5R,6S)-1-((S)-2-(tert-Butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid

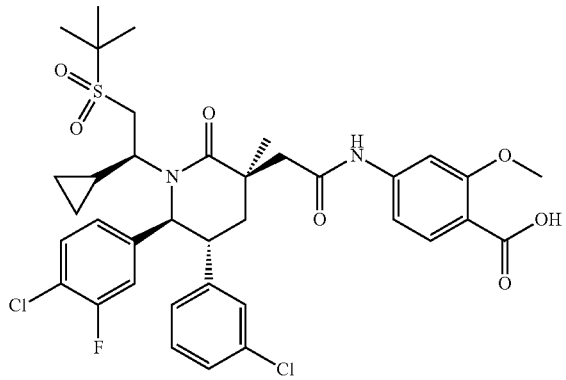 [SMILES: COc1cc(NC(=O)C[C@@]2(C)C[C@H](c3cccc(Cl)c3)[C@@H](c3ccc(Cl)c(F)c3)N([C@H](CS(=O)(=O)C(C)(C)C)C3CC3)C2=O)ccc1C(=O)O]

Step A. Methyl 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoate

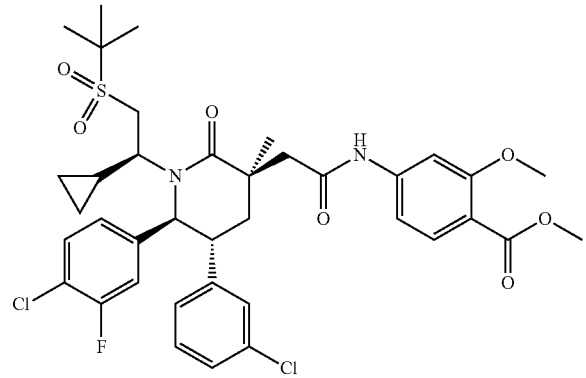 [SMILES: COC(=O)c1ccc(NC(=O)C[C@@]2(C)C[C@H](c3cccc(Cl)c3)[C@@H](c3ccc(Cl)c(F)c3)N([C@H](CS(=O)(=O)C(C)(C)C)C3CC3)C2=O)cc1OC]

N-(3-Dimethylaminopropyl)-N'-ethylcarbodiimide hydrochloride (EDC, 76 g, 398 mmol) was added to a mixture of 2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetic acid (79.4 g, 133 mmol, Example 4, Step J) and methyl 4-amino-2-methoxybenzoate (26.4 g, 146 mmol) in pyridine (332 mL) at 3° C. The mixture was allowed to warm to room temperature and was stirred at room temperature for 16 hours. The reaction mixture was cooled to 0° C. and added to an ice-cold solution of 1 M hydrochloric acid (1 L). Ether (1 L) was added and the layers were agitated and then separated. The organic layer was washed with 1 M hydrochloric acid (6×500 mL), saturated aqueous sodium bicarbonate (500 mL), brine (500 mL), dried over magnesium sulfate, filtered and concentrated under a vacuum to provide an off-white foam.

$^1$H NMR (400 MHz, CDCl$_3$, δ ppm): −1.20 to −1.12 (m, 1H), −0.35 to −0.20 (m, 1H), 0.05-0.20 (m, 1H), 0.32-0.45 (m, 1H), 1.45 (s, 9H), 1.48 (s, 3H), 1.86-1.98 (m, 1H), 2.03 (dd, J=2.7 and 13.7 Hz, 1H), 2.43 (t, J=13.7, 1H), 2.64-2.75 (m, 1H), 2.80 (d, J=14.3 Hz, 1H), 2.89-2.96 (m, 2H), 3.24 (dt, J=2.5 and 10.8 Hz, 1H), 3.89 (s, 3H), 3.96 (s, 3H), 4.28-4.36 (m, 1H), 4.98 (d, J=10.8 Hz, 1H), 6.85-6.93 (m, 3H), 6.99 (br s, 1H), 7.06-7.18 (m, 4H), 7.82 (br s, 1H), 7.85 (d, J=8.4 Hz, 1H), 8.81 (br s, 1H). MS (ESI) 761.2 [M+H]$^+$.

Step B. 4-(2-((3R,5R,6S)-1-((S)-2-(tert-Butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid

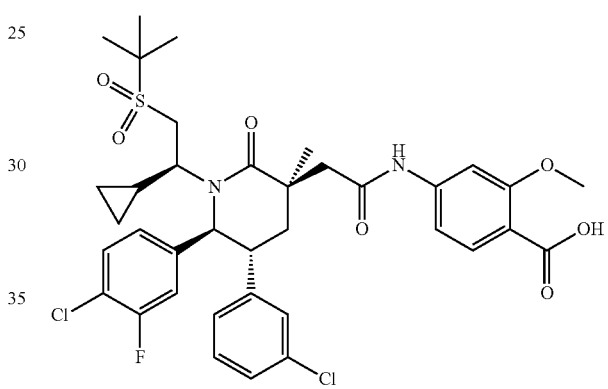

A solution of lithium hydroxide monohydrate (18.2 g, 433 mmol) in water (295 mL) was added to a solution of methyl 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoate (164.9 g, 217 mmol, Example 5, Step A) in tetrahydrofuran (591 mL) and methanol (197 mL) at room temperature. After stirring for 15 hours at room temperature, a trace amount of the ester remained, so the reaction mixture was heated at 50° C. for 1 hour. When the reaction was complete, the mixture was concentrated under a vacuum to remove the tetrahydrofuran and methanol. The thick mixture was diluted with water (1 L) and 1 M hydrochloric acid (1 L) was added. The resulting white solid was collected by vacuum filtration in a Büchner funnel. The vacuum was removed, and water (1 L) was added to the filter cake. The material was stirred with a spatula to suspend it evenly in the water. The liquid was then removed by vacuum filtration. This washing cycle was repeated three more times to provide a white solid. The solid was dried under vacuum at 45° C. for 3 days to provide the title compound as a white solid.

$^1$H NMR (500 MHz, DMSO-d$_6$) δ ppm −1.30 to −1.12 (m, 1H), −0.30 to −0.13 (m, 1H), 0.14-0.25 (m, 1H), 0.25-0.38 (m, 1H), 1.30 (s, 3H), 1.34 (s, 9H), 1.75-1.86 (m, 1H), 2.08-2.18 (m, 2H), 2.50-2.60 (m, 1H), 2.66 (d, J=13.7, 1H), 3.02-3.16 (m, 2H), 3.40-3.50 (m, 1H), 3.77 (s, 3H), 4.05-4.20 (m, 1H), 4.89 (d, J=10.5 Hz, 1H), 6.90-6.93 (m, 3H), 7.19 (d, J=8.8 Hz, 1H), 7.22-7.26 (m, 3H), 7.40-7.50 (m, 1H), 7.54 (br s, 1H), 7.68 (d, J=8.6 Hz, 1H) 10.44 (s, 1H), 12.29 (br s, 1H). MS (ESI) 747.2 [M+H]+.

BIOLOGICAL ASSAYS

Homogenous Time-Resolved Fluorescence Assay (HTRF1 and HTRF2 Assays)

The standard assay conditions for the in vitro HTRF assay consisted of a 50 µl total reaction volume in black 384-well Costar polypropylene plates in 1×PBS buffer pH 7.4, 1 mM DTT, 0.1% BSA, 2.5 nM GST-hMDM2 (aa 1-188), 5 nM biotinylated-p53 (aa 1-83), 1.8 nM SA-XLent (Cisbio; Bedford, Mass.), 0.6 nM anti-GST cryptate monoclonal antibody (Cisbio; Bedford, Mass.) and 200 mM KF. Amino acid residues 1-188 of human MDM2 were expressed as an amino-terminal glutathione S-transferase (GST) fusion protein (GST-hMDM2) in *Escherichia coli*. Residues 1-83 of human p53 were expressed as an amino-terminal AviTag™-TrxA-6× His fusion protein (biotinylated p53) in *E. coli*. Each protein was purified from cell paste by affinity chromatography.

Specifically, 10 µL of GST-hMDM2 was incubated with 10 ul of diluted compound (various concentrations, serially diluted) in 10% DMSO for 20 minutes at room temperature. 20 µL of biotinylated-p53 was added to the GST-hMDM2+ compound mixture, and then incubated at room temperature for 60 minutes. 10 µL of detection buffer consisting of SA-XLent, anti-GST cryptate antibody and KF was added to GST-hMDM2, biotinylated-p53 and compound reaction and left at room temperature to reach equilibrium for >4 hours. The final concentration of DMSO in the reaction was 2%. Time-resolved fluorescence readings were measured on a microplate multilabel reader. Percentage of inhibition was calculated relative to nutlin-3.

For the HTRF2 assay, all assay conditions remained the same as described above, with the exception of the following changes in reagent concentrations: 0.2 nM GST-hMDM2 (1-188), 0.5 nM biotinylated-p53 (1-83), 0.18 nM SA-XLent, and 100 mM KF.

EdU assay

SJSA-1 cells were plated at a density of $2.8 \times 10^3$ cells per well in 384-well cell culture plates in 40 µL of growth medium and incubated for 24 hours at 37° C. and 5% $CO_2$. The growth medium consisted of RPMI 1640 medium (Sigma-Aldrich, St. Louis, Mo.), supplemented with 10 mM HEPES, 1 mM sodium pyruvate, 1× Penicillin-Streptomycin, 2 mM Glutamine, and 10% FBS.

On the following day, the growth medium was removed and replaced with compound medium which consisted of RPMI 1640 supplemented with 10 mM HEPES, 1 mM sodium pyruvate, 1× Penicillin-Streptomycin, 2 mM Glutamine, and 10% human serum. Test compounds dissolved in DMSO were diluted in compound medium and added to the cells to a concentration range of 33 µM to 3 pM. The cells were treated with compounds for 16 hours at 37° C. and 5% $CO_2$ for 16 hours. On day 3, the Click-It EdU HCS assay was used to determine cell proliferation status after compound treatment. EdU dissolved in compound medium was added to cells to a final concentration of 10 µM. The cells were then incubated for 1 hour at 37° C. and 5% $CO_2$. After EdU labeling, Click-It EdU HCS assay procedures were performed according to the manufacturer's instructions with assay volumes reduced to 25 µL to adjust for 384 well formats. In short, cells were fixed by 4% formaldehyde and permeabilized with 0.1% Triton-X 100 in PBS. After washing with PBS, cells were treated sequentially with Click-It reaction buffer and NuclearMask™ Blue stain. Cells then were washed and imaged using an Opera High Content Screening System (PerkinElmer Life and Analytical Sciences). The percentage of EdU incorporated cells was calculated and used for $IC_{50}$ calculations.

Click-It EdU HCS assay kit was obtained from Life Technologies (Grand Island, N.Y.), RPMI1640, L-Glutamine, HEPES and Sodium Pyruvate were obtained from Cellgro (Manassas, Va.). 384-well cell culture plates were obtained from PerkinElmer Life and Analytical Sciences (Waltham, Mass.). FBS was obtained from HyClone/ThermoFisher Scientific (Logan, Utah), and human serum was obtained from Bioreclamation (Hicksville, N.Y.). The SJSA-1 cell line was obtained from ATCC (Manassas, Va.).

Values from DMSO-treated wells were normalized to POC (percent of control)=100, and no-EdU-labeled cells to POC=0. $IC_{50}$ values were determined by using the Genedata Screener V9.0.1. The curve fitting algorithm used for dose response data analysis in Genedata Screener is a custom implementation of a robust curve-fitting algorithm called ROUT (Robust regression with outlier detection) and uses a four-parameter logistical (4PL) Hill model, FIG. 1. This algorithm performs a robust, non-linear regression, analyzes the residuals of the data points to detect outliers, and then performs a simple curve fit ignoring data points previously defined as outliers.

Model:

$$y = S_{inf} + \frac{S_0 - S_{inf}}{1 + 10^{(\log AC_{50} - \log x) nHill}}$$

The ROUT implementation fits and returns the four fit parameters (So, Sin f, AC50 IP, nHill) and fit results (Max Activity, AC50 Transit) along with their 95% confidence intervals:

| Fit Parameter | Description |
| --- | --- |
| S0 | Signal in the absence of compound |
| Sinf | Signal at infinite compound concentrations |
| AC50 IP | Concentration at the point of inflection (relative AC50) |
| nHill | Hill parameter; Slope at the point of inflection |

| Result | Description |
| --- | --- |
| Max Activity | Value at the maximum (unmasked) concentration tested (cmax) |
| AC50 Transit | Concentration where the fitted curve crosses 50% activity (absolute AC50) |

Human Hepatocyte Intrinsic Clearance Assay

Cryopreserved human hepatocytes pooled from 20 donors (Celsis-In Vitro Technologies, Baltimore, Md.) were used to determine the intrinsic clearance of the Example compounds. The viabilities of the hepatocytes in incubations were 70 to 75%. Each Example compound was incubated at a concentration of 500 nM in a cell incubation medium (Celsis-InVitro Technologies, Baltimore, Md.) containing hepatocytes at a density of 1 million cells/mL. One aliquot of incubation mixture (100 µL) was prepared for each time point. The incubations were carried out in a 37° C. incubator under an atmosphere of 95% air and 5% $CO_2$ at 100% relative humidity with shaking at 1400 rpm. At 0, 5, 15, 30, 60 and 90 minutes, aliquots of incubation mixture were removed from the incubator, and quenched with acetonitrile containing 0.1% (v/v) formic acid and internal standard (7-hydroxy-4-trifluoromethylcoumarin). Samples were then centrifuged at 5700 rpm (6100 g) at 4° C. for 10 minutes. Supernatants were transferred to a sample plate, mixed with equal volume of water containing 0.1% formic acid, and analyzed using LC-MS/MS.

The LC-MS/MS system for sample analysis consisted of a reverse phase UHPLC (Shimadzu Model Nexera LC-30AD, Shimadzu Scientific Instruments, Inc, Columbia, Md.) interfaced with an API4000 triple quadruple mass spectrometer operating in negative ion mode (Applied Biosystems, Inc., Foster City, Calif.). Chromatographic separation was achieved using a Phenomenex Kinetex Luna $C_{18}$ column (Phenomenex, Torrance, Calif.) (2×50 mm, 2.6 µm) maintained at 55° C. with a mobile phase flow rate of 1.2 mL/min. The mobile phase consisted of 0.1% formic acid in water (A) and 0.1% formic acid in acetonitrile (B). A gradient elution program was applied as follows: an initial linearly increased from 95% A/5% B to 5% A/95% B in 0.8 minutes and held at 5% A/95% B for 0.2 min, then returned to 95% A/5% B in 0.1 minute and re-equilibrated at this composition for additional 0.5 minutes prior to the next injection. The appropriate multiple reaction monitoring (MRM) transition was used for the detection of each Example compound, and the MRM transition m/z 229.2→3 201.2 was used for the detection of internal standard (7-hydroxy-4-trifluoromethylcoumarin).

Intrinsic clearance ($CL_{int}$) was calculated from in vitro $t_{1/2}$ of the Example compound in hepatocyte incubation based on the following equations (Obach, 1997 and 1999):

$$CL_{int} = \frac{0.693}{t_{1/2}}$$

References For Human Hepatocyte Intrinsic Clearance Assay And Calculation

Ye Q., Jiang B. M., Chan H., Lixia J (in preparation for publication) Optimization of Hepatocyte Intrinsic Clearance Assay for Human Metabolic Clearance Prediction: Impact of Assay Conditions on Prediction Accuracy.

Obach R S (1997) Nonspecific binding to microsomes: impact on scale-up of in vitro intrinsic clearance to hepatic clearance as assessed through examination of warfarin, imipramine, and propranolol. *Drug Metab Dispos* 25: 1359-1369.

Obach R S (1999) Prediction of human clearance of twenty-nine drugs from hepatic microsomal intrinsic clearance data. An examination of in vitro half-live approach and nonspecific binding to microsomes. *Drug Metab Dispos* 27: 1350-1359.

Human Hepatocyte CYP1A2, CYP2B6, and CYP3A4 Induction Assay

Materials. Omeprazole, phenobarbital, rifampicin, dexamethasone, dimethyl sulphoxide (DMSO), Krebs Henseleit Buffer (KHB) (ingredients for KHB=0.30 g/L magnesium sulfate heptahydrate, 0.16 g/L potassium phosphate monobasic, 0.36 g/L potassium chloride, 6.95 g/L sodium chloride, 2.1 g/L sodium bicarbonate, 0.38 g/L calcium chloride dihydrate, 12.6 mM 4-(2-hydroxyethyl)-1-piperazineethanesulfonic acid (HEPES) in tissue culture water), phenacetin, acetaminophen, bupropion hydrochloride, testosterone, 6β-hydroxytestosterone, prazosin hydrochloride, cell-culture-grade water, Dulbecco's Modified Eagle's Medium (DMEM), and William's Medium E (WME) were purchased from Sigma-Aldrich (St. Louis, Mo.). Insulin-transferrin-selenium supplement (ITS), penicillin-streptomycin-L-glutamine supplement (PSG), fetal bovine serum (FBS), phosphate-buffered saline (PBS), cryopreserved hepatocyte recovery medium (CHRM), and three individual-donor lots of cryopreserved adult human hepatocytes were obtained from Life Technologies (Grand Island, N.Y.). Collagen I-precoated 24-well plates and hydroxybupropion were acquired from Becton Dickinson Labware (Bedford, Mass.). Branched DNA (b-DNA) probe sets for human CYP1A2, CYP2B6, CYP3A4, and 18S rRNA and the Panomics Discovery XL Kit were purchased from Affymetrix Inc. (Santa Clara, Calif.).

In vitro Methods. On Day 1, Hepatocyte Plating Medium (HPM) was prepared by supplementing DMEM to final concentrations of 1×PSG, 1×ITS, 0.1 µM dexamethasone, and 10% FBS. Formulation of Hepatocyte Maintenance Medium (HMM) was accomplished by supplementing WME to final concentrations of 1×PSG, 1×ITS, and 0.1 µM dexamethasone. Vials of cryopreserved human hepatocytes were thawed for 1.5 to 2 minutes by swirling gently in a 37° C. water bath, immediately placing each individual hepatocyte lot into a CHRM vial, and centrifuging at 100 g for 10 minutes at 25° C. The CHRM medium was removed from the pelleted hepatocytes, and each individual lot was gently resuspended in HPM. Each lot of hepatocytes was counted using a hemocytometer and diluted with HPM to a final concentration of 0.75×10$^6$ total cells/mL. The viability for each preparation was greater than or equal to 90%. Individual lots were plated in collagen-coated 24-well plates with approximately 0.38× 10$^6$ cells/well. The hepatocytes were placed in a 37° C. incubator (Steri-Cult $CO_2$ Incubator, Model 3310, Thermo Fisher Scientific, Waltham, Mass.) under an atmosphere of 95% air/5% $CO_2$ and 90% relative humidity, and cells were allowed a 3 to 6 hour attachment period. After the attachment period, the plating medium and unattached cells were removed by aspiration and 37° C. HMM was added to each well (0.5 mL/well), and the cells were incubated overnight. On Day 2, the medium was aspirated and fresh 37° C. HMM was reapplied to the cells for an overnight acclimation period. On Days 3 and 4, the medium was aspirated and fresh 37° C. HMM containing either DMSO (0.1%, vehicle control), omeprazole (50 µM, CYP1A2 positive control inducer), phenobarbital (1000 µM, CYP2B6 positive control inducer), rifampicin (10 µM, CYP3A4 positive control inducer), Examples 1 to 5 were applied to the wells (0.5 mL/well, N=3 wells/treatment/CYP isoform). The Example compounds to be tested were prepared in DMSO stock solutions resulting in final incubation concentrations of 0.1% DMSO. Example compound treatment was maintained for a total of 48 hours. On Day 5, the medium was aspirated, and the hepatocytes were gently washed one time with KHB (37° C., pH 7.4). The KHB was removed, and a second application of KHB was administered (0.5 mL/well). The hepatocytes were placed back into the incubator and allowed to acclimate to the KHB for 10 minutes. P450 enzyme activities were subsequently determined by the addition of marker substrates phenacetin (100 µM, CYP1A2 probe substrate, 30-minute incubation) bupropion hydrochloride (100 µM, CYP2B6 probe substrate, 20-minute incubation), and testosterone (200 µM, CYP3A4 probe substrate, 14-minute incubation) which were dissolved in KHB (37° C., pH 7.4, 0.5 mL/well). After the substrate incubation periods, the buffers were collected and stored at −80° C. until analyzed. Hepatocytes used for mRNA analysis were washed once in PBS (0.5 mL/well, 25° C., containing calcium and magnesium) and protocol-prepared b-DNA lysis buffer was added to each well (0.5 mL/well). The hepatocytes were lysed by gently pipetting the lysis buffer up and down five times, and the plates were stored at −80° C. until analysis.

P450 Activity Analysis. Analysis and quantification of acetaminophen, hydroxybupropion, and 6β-hydroxytestosterone (metabolites for the CYP1A2 metabolism of phenacetin, CYP2B6 metabolism of bupropion hydrochloride, and CYP3A4 metabolism of testosterone, respectively) was performed by liquid chromatography-tandem mass spectrometry on a system comprising a reverse phase high-performance liquid chromatograph (Shimadzu, Kyoto, Japan) and a triple quadrupole mass spectrometer (API 5000, Applied Biosystems, Foster City, Calif.) using Turbo Ion-Spray (Applied Biosystems) via multiple reaction monitoring. Specimens (25 μL) were loaded on a C18 column (Onyx Monolithic C18, 100×3.0 m; Phenomenex, Torrance, Calif.), and analytes were eluted with a linear gradient of mobile phase A (water with 0.1% acetic acid and 5% methanol) to B (water with 0.1% acetic acid and 95% methanol) in 4.6 minutes. The flow rate was 1 mL/min. The metabolites were quantified by comparison of peak area ratios of metabolite to internal standard (prazosin) to a standard curve prepared using authentic acetaminophen, hydroxybupropion, and 6β-hydroxytestosterone.

P450 mRNA Analysis. CYP1A2, CYP2B6, and CYP3A4 mRNA content was determined with branched DNA (b-DNA) signal amplification technology using the Panomics Discover XL Kit with assays performed according to the manufacturer's instructions. b-DNA probe sets containing capture extender, label extender, and blocking probes for human CYP1A2, CYP2B6, CYP3A4, and 18S rRNA were purchased from Affymetrix Inc. Plate washing steps were performed on an Elx405 automated microplate washer (BioTek Instruments Inc., Winooski, Vt.), and luminescence was analyzed on a Luminoskan Ascent microplate luminometer (Thermo Lab Systems, Helsinki, Finland). P450 mRNA levels were normalized to the mRNA levels of the housekeeping gene 18S rRNA.

Data Reporting. For each P450 isoform for mRNA analysis, fold increases over vehicle control (with vehicle control set to 1.0) were calculated for positive controls and each treatment group for the Example compounds. In addition, the percent of positive control was calculated for mRNA levels for all treatment groups according to the equation:

% positive control=[(activity of Example compound treated cells–activity of vehicle only treated cells)/(activity of positive control treated cells–activity of vehicle only treated cells)]×100

Assessment Criteria
None=<20% PC (positive control)
Moderate=20-39% PC
Potent=≥40% PC
mRNA Transcript Induction Assay Data
CYP1A2 or CYP2B6 data
  None of the compounds of Examples 1 to 5 showed induction of CYP 1A2 or CYP2B6.

| | CYP3A4 data | | |
|---|---|---|---|
| Treatment | mRNA % of Positive Control (Donor One) | mRNA % of PositiveControl (Donor Two) | mRNA % of Positive Control (Donor Three) |
| Example 1 | | | |
| 0.1% DMSO | 0.00 | 0.00 | 0.00 |
| 10 μM rifampicin | 100.00 | 100.00 | 100.00 |
| 0.1 μM | 4.75 | 5.44 | −0.11 |
| 1 μM | 2.97 | 5.69 | −0.57 |
| 10 μM | 8.31 | 14.46 | 2.06 |
| Example 2 | | | |
| 0.1% DMSO | 0.00 | 0.00 | 0.00 |
| 10 μM rifampicin | 100.00 | 100.00 | 100.00 |
| 0.1 μM | 0.42 | 2.99 | −0.37 |
| 1 μM | 5.40 | 8.42 | 3.39 |
| 10 μM | 29.62 | 44.51 | 33.84 |
| Example 3 | | | |
| 0.1% DMSO | 0.00 | 0.00 | 0.00 |
| 10 μM rifampicin | 100.00 | 100.00 | 100.00 |
| 0.1 μM | 1.71 | 4.95 | 0.15 |
| 1 μM | 17.15 | 10.38 | 3.21 |
| 10 μM | 37.77 | 45.78 | 37.60 |
| Example 4 | | | |
| 0.1% DMSO | 0.00 | 0.00 | 0.00 |
| 10 μM rifampicin | 100.00 | 100.00 | 100.00 |
| 0.1 μM | 1.62 | 2.30 | 0.42 |
| 1 μM | 2.96 | 7.29 | 0.47 |
| 10 μM | 10.14 | 12.51 | 3.07 |

| Treatment | mRNA % of Positive Control (one donor) |
|---|---|
| Example 5 | |
| 0.1% DMSO | 0.00 |
| 10 μM rifampicin | 100.00 |
| 0.1 μM | −1.49 |
| 1 μM | 0.34 |
| 10 μM | 0.98 |

-continued
| | CYP3A4 data | |
|---|---|---|
| | Ex. 1 | Ex. 4 |
| | 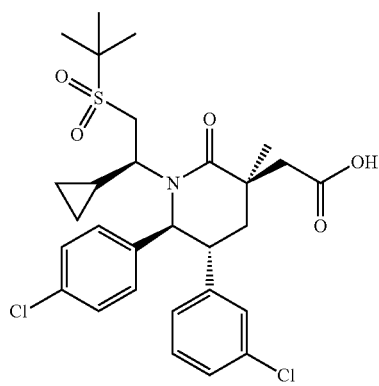 [SMILES: CC(C)(C)S(=O)(=O)C[C@H](C1CC1)N1C(=O)[C@@](C)(CC(=O)O)C[C@H](c2cccc(Cl)c2)[C@H]1c1ccc(Cl)cc1] | 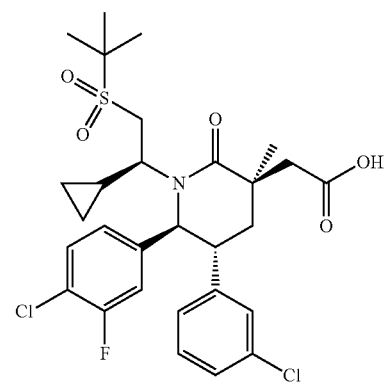 [SMILES: CC(C)(C)S(=O)(=O)C[C@H](C1CC1)N1C(=O)[C@@](C)(CC(=O)O)C[C@H](c2cccc(Cl)c2)[C@H]1c1ccc(Cl)c(F)c1] |
| HTRF2 assay IC$_{50}$ (μM) | 0.0000962 | 0.000102 |
| Cellular (SJSA-1) EdU assay IC$_{50}$ (μM) 10% human serum | 0.0016 | 0.0012 |
| Human hepatocyte CL$_{int}$ assay (μL/min/10$^6$ cells) | 16 | 26 |
| Induction Assay Summary | None | None |
| | Ex. 5 |
|---|---|
| | 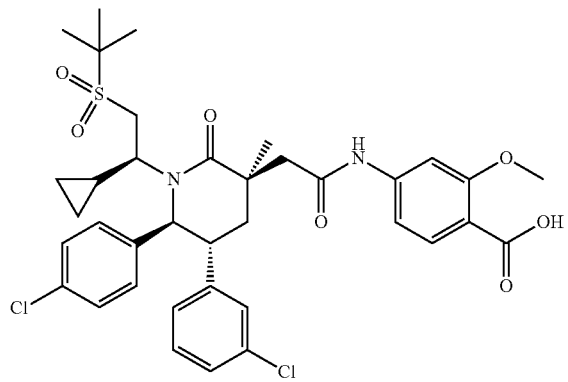 [SMILES: COc1cc(NC(=O)C[C@@]2(C)C[C@H](c3cccc(Cl)c3)[C@@H](c3ccc(Cl)cc3)N([C@H](CS(=O)(=O)C(C)(C)C)C3CC3)C2=O)ccc1C(=O)O] |
| HTRF2 assay IC$_{50}$ (μM) | 0.0000503 |
| Cellular (SJSA-1) EdU assay IC$_{50}$ (μM) 10% human serum | 0.0017 |
| Human hepatocyte CL$_{int}$ assay (μL/min/10$^6$ cells) | 1.45 |
| Induction Assay Summary | None |

CYP3A4 data

| | Ex. 1 | Ex. 2 |
|---|---|---|
| | 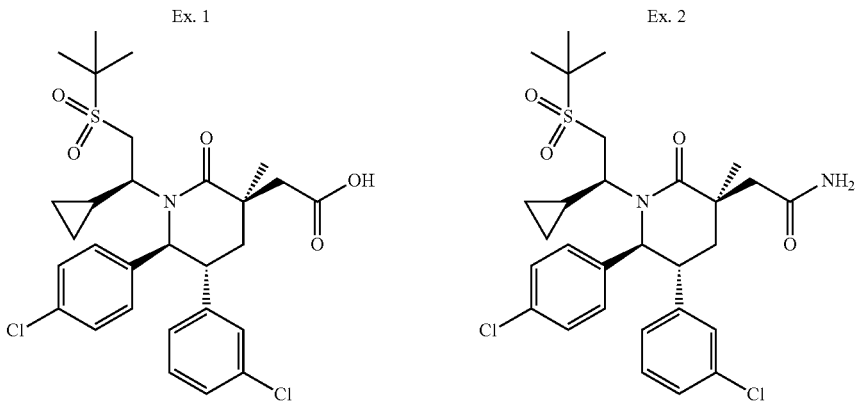 | |
| HTRF2 assay $IC_{50}$ (μM) | 0.0000962 | 0.00183 |
| Cellular (SJSA-1) EdU assay $IC_{50}$ (μM) 10% human serum | 0.0016 | 0.033 |
| Human hepatocyte $CL^{int}$ assay (μL/min/$10^6$ cells) | 16 | 26 |
| Induction Assay Summary | None | CYP3A4 |

| | Ex. 3 | Ex. 5 |
|---|---|---|
| | 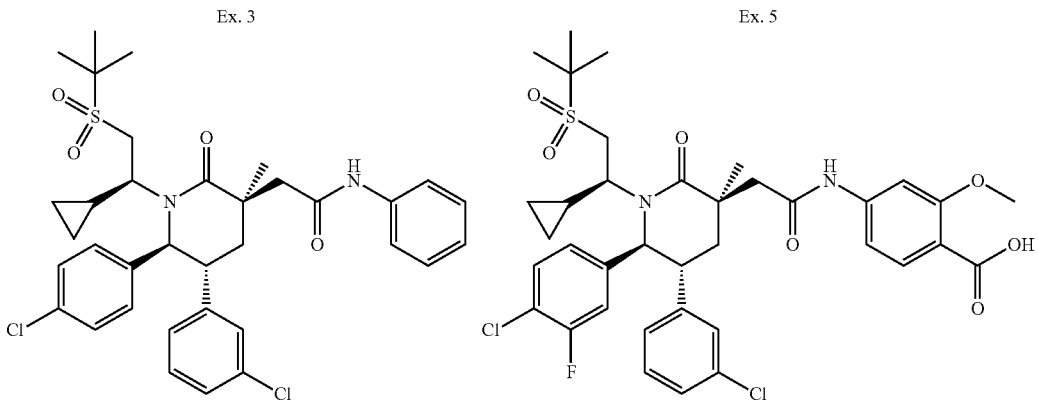 | |
| HTRF2 assay $IC_{50}$ (μM) | 0.00033 | 0.0000503 |
| Cellular (SJSA-1) EdU assay $IC_{50}$ (μM) 10% human serum | 0.0846 | 0.0017 |
| Human hepatocyte $CL^{int}$ assay (μL/min/$10^6$ cells) | 28 | 1.45 |
| Induction Assay Summary | CYP3A4 | None |

None means the compound tested did not induce expression of CYP1A2, CYP2B6 or CYP3A4.
CYP3A4 means the compound induced expression of CYP3A4.

The addition of a fluorine group to the compound of Example 1 to make Example 4 results in higher human hepatocyte clearance than the compound of Example 1. In view of this data, it was surprising and unexpected that the compound of Example 5, which also contains a fluorine group, shows lower human hepatocyte clearance than either of the compounds of Examples 1 or 4.

In addition, when the carboxylic acid functional group of Example 1 is converted to an amide (Example 2), the hepatocyte clearance increases and further increases when a phenyl amide derivative is made (Example 3). Furthermore, both of Examples 2 and 3 exhibit CYP3A4 mRNA induction. It is further surprising and unexpected that the compound of Example 5, which contains both a fluorine group and a derivatized phenyl amide functional group, does not show CYP3A4 mRNA induction and further shows lower human hepatocyte clearance than any of Examples 1 to 4. It is noted that human hepataocyte clearance data and CYP3A4 mRNA induction data is used by those skilled in the art to help select appropriate compounds for human therapy.

What is claimed is:
1. The compound

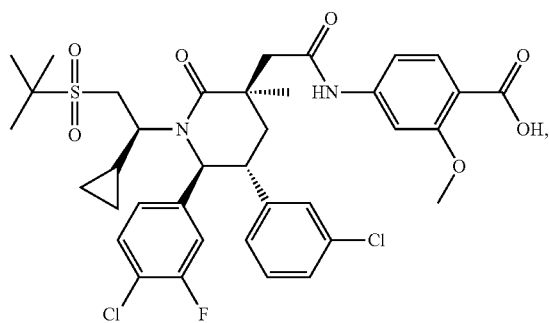 [SMILES: COc1cc(NC(=O)C[C@@]2(C)C[C@H](c3cccc(Cl)c3)[C@@H](c3ccc(Cl)c(F)c3)N([C@H](CS(=O)(=O)C(C)(C)C)C3CC3)C2=O)ccc1C(=O)O]

or a pharmaceutically acceptable salt thereof.
2. The compound

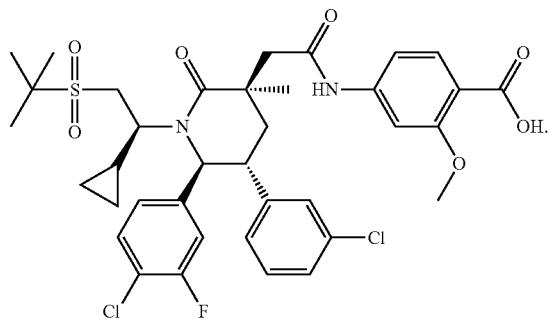 [SMILES: COc1cc(NC(=O)C[C@@]2(C)C[C@H](c3cccc(Cl)c3)[C@@H](c3ccc(Cl)c(F)c3)N([C@H](CS(=O)(=O)C(C)(C)C)C3CC3)C2=O)ccc1C(=O)O]

3. A pharmaceutical composition comprising a compound of any one of claim 1 or 2, and a pharmaceutically acceptable excipient.
4. A method of treating cancer in a subject in need thereof, the method comprising administering to the subject an effective dosage amount of a compound according to any one of claims 1 to 2.
5. The method of claim 4, wherein the cancer is selected from bladder, breast, colon, rectum, kidney, liver, small cell lung cancer, non-small-cell lung cancer, esophagus, gallbladder, ovary, pancreas, stomach, cervix, thyroid, prostate, skin, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, acute or chronic myelogenous leukemia, melanoma, endometrial cancer, head and neck cancer, glioblastoma, or osteosarcoma.
6. The method of claim 4, wherein the cancer is bladder cancer.
7. The method of claim 4, wherein the cancer is breast cancer.
8. The method of claim 4, wherein the cancer is colon cancer.
9. The method of claim 4, wherein the cancer is rectum cancer.
10. The method of claim 4, wherein the cancer is kidney cancer.
11. The method of claim 4, wherein the cancer is liver cancer.
12. The method of claim 4, wherein the cancer is small cell lung cancer.
13. The method of claim 4, wherein the cancer is non-small-cell lung cancer.
14. The method of claim 4, wherein the cancer is esophagus cancer.
15. The method of claim 4, wherein the cancer is gallbladder cancer.
16. The method of claim 4, wherein the cancer is ovary cancer.
17. The method of claim 4, wherein the cancer is pancreas cancer.
18. The method of claim 4, wherein the cancer is stomach cancer.
19. The method of claim 4, wherein the cancer is cervix cancer.
20. The method of claim 4, wherein the cancer is thyroid cancer.
21. The method of claim 4, wherein the cancer is prostate cancer.
22. The method of claim 4, wherein the cancer is skin cancer.
23. The method of claim 4, wherein the cancer is acute lymphocytic leukemia.
24. The method of claim 4, wherein the cancer is chronic myelogenous leukemia.
25. The method of claim 4, wherein the cancer is acute lymphoblastic leukemia.
26. The method of claim 4, wherein the cancer is B-cell lymphoma.
27. The method of claim 4, wherein the cancer is T-cell-lymphoma.
28. The method of claim 4, wherein the cancer is Hodgkin's lymphoma.
29. The method of claim 4, wherein the cancer is non-Hodgkin's lymphoma.
30. The method of claim 4, wherein the cancer is hairy cell lymphoma.
31. The method of claim 4, wherein the cancer is Burkett's lymphoma.
32. The method of claim 4, wherein the cancer is acute myelogenous leukemia.
33. The method of claim 4, wherein the cancer is chronic myelogenous leukemia.
34. The method of claim 4, wherein the cancer is identified as p53 wildtype.
35. The method of claim 4, wherein the cancer is endometrial cancer.
36. The method of claim 4, wherein the cancer is head and neck cancer.

37. The method of claim 4, wherein the cancer is glioblastoma.

38. The method of claim 4, wherein the cancer is osteosarcoma.

39. The method of claim 4, wherein the cancer is identified as p53 wildtype.

\* \* \* \* \*